(12) United States Patent
Collier et al.

(10) Patent No.: US 9,849,174 B2
(45) Date of Patent: *Dec. 26, 2017

(54) METHODS AND COMPOSITIONS RELATED TO IMMUNOGENIC FIBRILS

(71) Applicants: The Board of Regents of the University of Texas System, Austin, TX (US); University of Chicago, Chicago, IL (US)

(72) Inventors: Joel H. Collier, Chicago, IL (US); Jai S Rudra, Galveston, TX (US)

(73) Assignees: THE BOARD OF REGENTS OF THE UNIVERSITY OF TEXAS SYSTEM, Austin, TX (US); THE UNIVERSITY OF CHICAGO, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/866,344

(22) Filed: Sep. 25, 2015

(65) Prior Publication Data
US 2016/0074509 A1 Mar. 17, 2016

Related U.S. Application Data

(63) Continuation-in-part of application No. 13/540,863, filed as application No. PCT/US2010/057480 on Nov. 19, 2010, now Pat. No. 9,241,987.

(60) Provisional application No. 62/055,281, filed on Sep. 25, 2014, provisional application No. 61/263,213, filed on Nov. 20, 2009.

(51) Int. Cl.
| | |
|---|---|
| *A61K 39/00* | (2006.01) |
| *A61K 39/02* | (2006.01) |
| *A61K 39/38* | (2006.01) |
| *A61K 39/39* | (2006.01) |
| *A61K 39/015* | (2006.01) |
| *A61K 39/385* | (2006.01) |
| *A61K 47/64* | (2017.01) |
| *B82Y 5/00* | (2011.01) |

(52) U.S. Cl.
CPC ............ *A61K 39/39* (2013.01); *A61K 39/015* (2013.01); *A61K 39/385* (2013.01); *A61K 47/646* (2017.08); *A61K 2039/55516* (2013.01); *A61K 2039/6031* (2013.01); *A61K 2039/627* (2013.01); *A61K 2039/64* (2013.01); *A61K 2039/645* (2013.01); *B82Y 5/00* (2013.01)

(58) Field of Classification Search
CPC .... A61K 39/00; A61K 39/02; A61K 2039/64; A61K 2039/6031
USPC .................. 424/9.1, 9.2, 184.1, 185.1, 234.1; 530/300, 350
See application file for complete search history.

(56) References Cited

U.S. PATENT DOCUMENTS

| | | | |
|---|---|---|---|
| 4,578,770 A | 3/1986 | Mitani ...................... | 250/559.2 |
| 4,596,792 A | 6/1986 | Vyas .......................... | 424/185.1 |
| 4,599,230 A | 7/1986 | Milich et al. .............. | 424/189.1 |
| 4,599,231 A | 7/1986 | Milich et al. .............. | 424/189.1 |
| 4,601,903 A | 7/1986 | Frasch ....................... | 424/250.1 |
| 4,608,251 A | 8/1986 | Mia ............................ | 424/185.1 |
| 6,261,569 B1 | 7/2001 | Comis et al. .............. | 424/204.1 |
| 6,733,754 B2 | 5/2004 | Roberts et al. ............ | 424/184.1 |
| 6,793,923 B2 | 9/2004 | Brown et al. .............. | 424/184.1 |

OTHER PUBLICATIONS

Aggeli et al., "Responsive gels formed by the spontaneous self-assembly of peptides into polymeric beta-sheet tapes", *Nature*, 386:259-262, 1997.
Bettahi et al., "Antitumor activity of a self-adjuvanting glyco-lipopeptide vaccine bearing B cell, CD4+ and CD8+ T cell epitopes", *Cancer Immunol. Immunother.*, 58:187-200, 2009.
Bowerman, et al., "Self-assembly of amphipathic β-sheet peptides: insights and applications", *Biopolymers* 2012;98(3):169-84.
Cao et al., "Successful adjuvant-free vaccination of BALB/c mice with mutated amyloid beta peptides", *Neurosci.*, 9:25, 2008.
Chesson, et al., "Antigenic peptide nanofibers elicit adjuvant-free CD8+ T Cell Responses", *Vaccine*, 32: 1174-80, 2014.
Collier and Messersmith, "Enzymatic modification of self-assembled peptide structures with tissue transglutaminase", *Bioconjug. Chem.*, 14:748-755, 2003.
Collier, et al., "Multi-component extracellular matrices based on peptide self-assembly", *Chem Soc Rev* 2010;39(9):3413-24.
Collier, "Modular self-assembling biomaterials for directing cellular responses", *Soft Matter*, 4:2310-2315, 2008.
Davis et al., "Injectable self-assembling peptide nanofibers create intramyocardial microenvironments for endothelial cells", *Circulation*, 111:442-450, 2005.
Dubois et al., "Self-assembling peptide nanofibers and skeletal myoblast transplantation in infarcted myocardium", *J. Biomed. Mater. Res. B Appl. Biomater.*, 87:222-228, 2008.
Fisher, et al., "Free D-aspartate and D-alanine in normal and Alzheimer brain", *Brain Res Bull* 1991;26(6):983-85.
Genove et al., "The effect of functionalized self-assembling peptide scaffolds on human aortic endothelial cell function", *Biomaterials*, 26:3341-3351, 2005.
Gras et al., "Functionalised amyloid fibrils for roles in cell adhesion", *Biomaterials*, 29:1553-1562, 2008.
Guler et al., "Presentation of RGDS epitopes on self-assembled nanofibers of branched peptide amphiphiles", *Biomacromolecules*, 7:1855-1863, 2006.
Hartgerink et al., "Self-assembly and mineralization of peptide-amphiphile nanofibers", *Science*, 294:1684-1688, 2001.
Holmes et al., "Extensive neurite outgrowth and active synapse formation on self-assembling peptide scaffolds", *Proc. Natl. Acad. Sci. USA*, 97:6728-6733, 2000.

(Continued)

*Primary Examiner* — Rodney P Swartz
(74) *Attorney, Agent, or Firm* — Norton Rose Fulbright US LLP

(57) ABSTRACT

Embodiments of the invention are directed to fibrillar adjuvants. Epitopes assembled into nanofibers by a short synthetic fibrillization domain elicited high antibody titers in the absence of any adjuvant.

19 Claims, 16 Drawing Sheets

(56) References Cited

OTHER PUBLICATIONS

Horii et al., "Biological designer self-assembling peptide nanofiber scaffolds significantly enhance osteoblast proliferation, differentiation and 3-D migration", *PLoS One*:2:e190, 2007.

Hsieh et al., "Controlled delivery of PDGF-BB for myocardial protection using injectable self-assembling peptide nanofibers", *J. Clin. Invest.*, 116:237-248, 2006.

Huang, et al., "A totally synthetic, self-assembling, adjuvant-free MUC1 glycopeptide vaccine for cancer therapy", *J Am Chem Soc* 2012;134(21):8730-33.

Hudalla, et al., "A self-adjuvanting supramolecular vaccine carrying a folded protein antigen"*Adv Healthc Mater* 2013;2(8):1114-19.

Jung et al., "Modulating the mechanical properties of self-assembled peptide hydrogels via native chemical ligation", *Biomaterials*, 29:2143-2151, 2008.

Jung et al., "Co-assembling peptides as defined matrices for endothelial cells", *Biomaterials*, 30:2400-2410, 2009.

Lutolf and Hubbell, "Synthetic biomaterials as instructive extracellular microenvironments for morphogenesis in tissue engineering", *Nat. Biotechnol.*, 23:47-55, 2005.

Maude, et al., "Biomimetic self-assembling peptides as scaffolds for soft tissue engineering", *Nanomedicine* 2013;8(5):823-47.

Place et al., "Complexity in biomaterials for tissue engineering", *Nat. Mater.*, 8:457-470, 2009.

Riley et al., "Bioproduction and characterization of a pH responsive self-assembling peptide", *Biotechnol. Bioeng.*, 103:241-251, 2009.

Robertson et al., "DO11.10 and OT-II T Cells Recognize a C-Terminal Ovalbumin 323-339 Epitope", *Journal of Immunology*, 164:4706-4712, 2000.

Rudra, et al., "Modulating adaptive immune responses to peptide self-assemblies", *ACS Nano* 2012;6(2):1557-64.

Rudra, et al., "Self-assembled peptide nanofibers raising durable antibody responses against a malaria epitope", *Biomaterials* 2012;33(27):6476-84.

Rudra, et al., "A self-assembling peptide acting as an immune adjuvant", *Proc Natl Acad Sci U S A* 2010;107(2):622-67.

Schneider et al., "Responsive hydrogels from the intramolecular folding and self-assembly of a designed peptide", *J. Am. Chem. Soc.*, 124:15030-15037, 2002.

Silva et al., "Selective differentiation of neural progenitor cells by high-epitope density nanofibers", *Science*, 303:1352-1355, 2004.

Toth et al., "Recent Advances in Design and Synthesis of Self-Adjuvanting Lipopeptide Vaccines", *Int. J. Pept. Res. Ther.*, 14:333-340, 2008.

Tysseling-Mattiace et al., "Self-assembling nanofibers inhibit glial scar formation and promote axon elongation after spinal cord injury", *J. Neurosci.*, 28:3814-3823, 2008.

Yang and Mine, "Novel T-cell epitopes of ovalbumin in BALB/c mouse: potential for peptide-immunotherapy", *Biochem. Biophys. Res. Commun.*, 378:203-208, 2009.

Zhou et al., "Self-assembled peptide-based hydrogels as scaffolds for anchorage-dependent cells", *Biomaterials*, 30:2523-2530, 2009.

SEQUENCE LISTING

```
<160> NUMBER OF SEQ ID NOS: 67

<210> SEQ ID NO 1
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 1

Gln Gln Lys Phe Gln Phe Gln Phe Glu Gln Gln
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 2

Lys Phe Gln Phe Gln Phe Glu
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 3

Gln Gln Arg Phe Gln Phe Gln Phe Glu Gln Gln
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 4

Gln Gln Arg Phe Gln Trp Gln Phe Glu Gln Gln
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 5

Phe Glu Phe Glu Phe Lys Phe Lys Phe Glu Phe Glu Phe Lys Phe Lys
1               5                   10                  15

<210> SEQ ID NO 6
```

```
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 6

Gln Gln Arg Phe Glu Trp Glu Phe Glu Gln Gln
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: X is Ornithine
<220> FEATURE:
<221> NAME/KEY: MISC_FEATURE
<222> LOCATION: (5)..(5)
<223> OTHER INFORMATION: X is Ornithine
<220> FEATURE:
<221> NAME/KEY: MISC_FEATURE
<222> LOCATION: (7)..(7)
<223> OTHER INFORMATION: X is Ornithine

<400> SEQUENCE: 7

Gln Gln Xaa Phe Xaa Trp Xaa Phe Gln Gln Gln
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 8

Phe Lys Phe Glu Phe Lys Phe Glu Phe Lys Phe Glu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 9

Phe Lys Phe Gln Phe Lys Phe Gln Phe Lys Phe Gln
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 10

Ala Glu Ala Lys Ala Glu Ala Lys Ala Glu Ala Lys Ala Glu Ala Lys
1               5                   10                  15

<210> SEQ ID NO 11
<211> LENGTH: 16
<212> TYPE: PRT
```

<213> ORGANISM: Artificial Sequence
<220> FEATURE:
<223> OTHER INFORMATION: Synthetic Peptide

<400> SEQUENCE: 11

Ala Glu Ala Glu Ala Lys Ala Lys Ala Glu Ala Glu Ala Lys Ala Lys
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 12

Ala Glu Ala Glu Ala Glu Ala Glu Ala Lys Ala Lys Ala Lys Ala Lys
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 13

Arg Ala Asp Ala Arg Ala Asp Ala Arg Ala Asp Ala Arg Ala Asp Ala
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 14

Arg Ala Arg Ala Asp Ala Asp Ala Arg Ala Arg Ala Asp Ala Asp Ala
1               5                   10                  15

<210> SEQ ID NO 15
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 15

Ser Gly Arg Gly Tyr Asx Leu Gly Gly Gln Gly Ala Gly Ala Ala Ala
1               5                   10                  15

Ala Ala Gly Gly Ala Gly Gln Gly Gly Tyr Gly Gly Leu Gly Ser Gln
                20                  25                  30

Gly

<210> SEQ ID NO 16
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: X is Val, Ala, Ser or Pro
<220> FEATURE:
<221> NAME/KEY: MISC_FEATURE
<222> LOCATION: (6)..(6)
<223> OTHER INFORMATION: X is Val, Ala, Ser or Pro
<220> FEATURE:
<221> NAME/KEY: MISC_FEATURE
<222> LOCATION: (8)..(8)
<223> OTHER INFORMATION: X is Val, Ala, Ser or Pro
<220> FEATURE:
<221> NAME/KEY: MISC_FEATURE
<222> LOCATION: (10)..(10)
<223> OTHER INFORMATION: X is Val, Ala, Ser or Pro

<400> SEQUENCE: 16

Glu Trp Glu Xaa Glu Xaa Glu Xaa Glu Xaa
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: X is Val, Ala, Ser or Pro
<220> FEATURE:
<221> NAME/KEY: MISC_FEATURE
<222> LOCATION: (5)..(5)
<223> OTHER INFORMATION: X is Val, Ala, Ser or Pro
<220> FEATURE:
<221> NAME/KEY: MISC_FEATURE
<222> LOCATION: (7)..(7)
<223> OTHER INFORMATION: X is Val, Ala, Ser or Pro
<220> FEATURE:
<221> NAME/KEY: MISC_FEATURE
<222> LOCATION: (9)..(9)
<223> OTHER INFORMATION: X is Val, Ala, Ser or Pro

<400> SEQUENCE: 17

Trp Lys Xaa Lys Xaa Lys Xaa Lys Xaa Lys
1               5                   10

<210> SEQ ID NO 18
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 18

Lys Trp Lys Val Lys Val Lys Val Lys Val Lys Val Lys Val Lys
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 19

Leu Leu Leu Leu Lys Lys Lys Lys Lys Lys Lys Leu Leu Leu Leu
1               5                   10                  15

<210> SEQ ID NO 20
<211> LENGTH: 21
<212> TYPE: PRT
<213> ORGANISM: Artificial Sequence
<220> FEATURE:
<223> OTHER INFORMATION: Synthetic Peptide

```
<400> SEQUENCE: 20

Val Lys Val Lys Val Lys Val Lys Val Asp Pro Pro Thr Lys Val Lys
1               5                   10                  15

Val Lys Val Lys Val
            20

<210> SEQ ID NO 21
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 21

Val Lys Val Lys Val Lys Val Lys Val Asp Pro Pro Thr Lys Val Lys
1               5                   10                  15

Thr Lys Val Lys Val
            20

<210> SEQ ID NO 22
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 22

Lys Val Lys Val Lys Val Lys Val Asp Pro Pro Ser Val Lys Val
1               5                   10                  15

Lys Val Lys Val Lys
            20

<210> SEQ ID NO 23
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 23

Val Lys Val Lys Val Lys Val Lys Val Asp Pro Pro Ser Lys Val Lys
1               5                   10                  15

Val Lys Val Lys Val
            20

<210> SEQ ID NO 24
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 24

Val Lys Val Lys Val Lys Thr Lys Val Asp Pro Pro Thr Lys Val Lys
1               5                   10                  15

Thr Lys Val Lys Val
            20

<210> SEQ ID NO 25
<211> LENGTH: 8
<212> TYPE: PRT
<213> ORGANISM: Artificial Sequence
<220> FEATURE:
<223> OTHER INFORMATION: Synthetic Peptide
```

```
<400> SEQUENCE: 25

Phe Lys Phe Glu Phe Lys Phe Glu
1               5

<210> SEQ ID NO 26
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 26

Ile Ser Gln Ala Val His Ala Ala His Ala Glu Ile Asn Glu Ala Gly
1               5                   10                  15

Arg

<210> SEQ ID NO 27
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 27

Asn Ala Asn Pro Asn Ala Asn Pro Asn Ala Asn Pro Ser Gly Ser Gly
1               5                   10                  15

Gln Gln Lys Phe Gln Phe Gln Phe Glu Gln Gln
            20                  25

<210> SEQ ID NO 28
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 28

Ile Ser Gln Ala Val His Ala Ala His Ala Glu Ile Asn Glu Ala Gly
1               5                   10                  15

Arg Ser Gly Ser Gly Gln Gln Lys Phe Gln Phe Gln Phe Glu Gln Gln
            20                  25                  30

<210> SEQ ID NO 29
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 29

Arg Ala Asp Ala Arg Ala Asp Ala Arg Ala Asp Ala Arg Ala Asp Ala
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 30

Arg Ala Asp Ala Arg Gly Asp Ala Arg Ala Asp Ala Arg Gly Asp Ala
1               5                   10                  15
```

<210> SEQ ID NO 31
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 31

Arg Ala Asp Ala Arg Ala Asp Ala
1               5

<210> SEQ ID NO 32
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 32

Arg Ala Arg Ala Asp Ala Asp Ala Arg Ala Arg Ala Asp Ala Asp Ala
1               5                   10                  15

<210> SEQ ID NO 33
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 33

Arg Ala Arg Ala Asp Ala Asp Ala
1               5

<210> SEQ ID NO 34
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 34

Ala Glu Ala Lys Ala Glu Ala Lys Ala Glu Ala Lys Ala Glu Ala Lys
1               5                   10                  15

<210> SEQ ID NO 35
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 35

Ala Glu Ala Lys Ala Glu Ala Lys
1               5

<210> SEQ ID NO 36
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 36

Arg Ala Glu Ala Arg Ala Glu Ala Arg Ala Glu Ala Arg Ala Glu Ala
1               5                   10                  15

```
<210> SEQ ID NO 37
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 37

Arg Ala Glu Ala Arg Ala Glu Ala
1               5

<210> SEQ ID NO 38
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 38

Lys Ala Asp Ala Lys Ala Asp Ala Lys Ala Asp Ala Lys Ala Asp Ala
1               5                   10                  15

<210> SEQ ID NO 39
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 39

Lys Ala Asp Ala Lys Ala Asp Ala
1               5

<210> SEQ ID NO 40
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 40

Ala Glu Ala Glu Ala His Ala His Ala Glu Ala Glu Ala His Ala His
1               5                   10                  15

Ala

<210> SEQ ID NO 41
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 41

Ala Glu Ala Glu Ala His Ala His Ala
1               5

<210> SEQ ID NO 42
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 42

Phe Glu Phe Glu Phe Lys Phe Lys Phe Glu Phe Glu Phe Lys Phe Lys
1               5                   10                  15
```

<210> SEQ ID NO 43
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 43

Phe Glu Phe Lys Phe Glu Phe Lys
1               5

<210> SEQ ID NO 44
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 44

Leu Glu Leu Glu Leu Lys Leu Lys Leu Glu Leu Glu Leu Lys Leu Lys
1               5                   10                  15

<210> SEQ ID NO 45
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 45

Leu Glu Leu Glu Leu Lys Leu Lys
1               5

<210> SEQ ID NO 46
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 46

Ala Glu Ala Glu Ala Lys Ala Lys Ala Glu Ala Glu Ala Lys Ala Lys
1               5                   10                  15

<210> SEQ ID NO 47
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 47

Ala Glu Ala Glu Ala Glu Ala Glu Ala Lys Ala Lys
1               5                   10

<210> SEQ ID NO 48
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 48

Ala Glu Ala Glu Ala Lys Ala Lys
1               5

```
<210> SEQ ID NO 49
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 49

Lys Ala Lys Ala Lys Ala Lys Ala Glu Ala Glu Ala Glu Ala Glu Ala
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 50

Ala Glu Ala Glu Ala Glu Ala Glu Ala Lys Ala Lys Ala Lys Ala Lys
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 51

Arg Ala Arg Ala Arg Ala Arg Ala Asp Ala Asp Ala Asp Ala Asp Ala
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 52

Ala Asp Ala Asp Ala Asp Ala Asp Ala Arg Ala Arg Ala Arg Ala Arg
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 53

Asp Ala Asp Ala Asp Ala Asp Ala Arg Ala Arg Ala Arg Ala Arg Ala
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 54

His Glu His Glu His Lys His Lys His Glu His Glu His Lys His Lys
1               5                   10                  15

<210> SEQ ID NO 55
```

<211> LENGTH: 8
<212> TYPE: PRT
<213> ORGANISM: Artificial Sequence
<220> FEATURE:
<223> OTHER INFORMATION: Synthetic Peptide

<400> SEQUENCE: 55

His Glu His Glu His Lys His Lys
1               5

<210> SEQ ID NO 56
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 56

Val Glu Val Glu Val Glu Val Glu Val Glu Val Glu Val Glu Val Glu
1               5                   10                  15

Val Glu Val Glu
            20

<210> SEQ ID NO 57
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 57

Arg Phe Arg Phe Arg Phe Arg Phe Arg Phe Arg Phe Arg Phe Arg Phe
1               5                   10                  15

Arg Phe Arg Phe
            20

<210> SEQ ID NO 58
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 58

Ile Ser Gln Ala Val His Ala Ala His Ala
1               5                   10

<210> SEQ ID NO 59
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 59

Ser Ile Ile Asn Phe Glu Lys Leu
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 60

```
Gly Gly Ala Ala Tyr
1               5

<210> SEQ ID NO 61
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 61

Ser Gly Ser Gly
1

<210> SEQ ID NO 62
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: REPEAT
<222> LOCATION: (1)..(4)
<223> OTHER INFORMATION: Repeat 1-50 times

<400> SEQUENCE: 62

Phe Lys Phe Glu
1

<210> SEQ ID NO 63
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Phe
<220> FEATURE:
<221> NAME/KEY: MISC_FEATURE
<222> LOCATION: (4)..(4)
<223> OTHER INFORMATION: D-Glu
<220> FEATURE:
<221> NAME/KEY: MISC_FEATURE
<222> LOCATION: (5)..(5)
<223> OTHER INFORMATION: D-Phe
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-Phe
<220> FEATURE:
<221> NAME/KEY: MISC_FEATURE
<222> LOCATION: (8)..(8)
<223> OTHER INFORMATION: D-Glu

<400> SEQUENCE: 63

Phe Lys Phe Glu Phe Lys Phe Glu
1               5
```

```
<210> SEQ ID NO 64
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 64

Phe Lys Phe Glu Phe Lys Phe Glu Gly Gly Ala Ala Tyr Ser Ile Ile
1               5                   10                  15

Asn Phe Glu Lys Leu
            20

<210> SEQ ID NO 65
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (3)..(3)
<223> OTHER INFORMATION: D-Phe
<220> FEATURE:
<221> NAME/KEY: MISC_FEATURE
<222> LOCATION: (4)..(4)
<223> OTHER INFORMATION: D-Glu
<220> FEATURE:
<221> NAME/KEY: MISC_FEATURE
<222> LOCATION: (5)..(5)
<223> OTHER INFORMATION: D-Phe
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (7)..(7)
<223> OTHER INFORMATION: D-Phe
<220> FEATURE:
<221> NAME/KEY: MISC_FEATURE
<222> LOCATION: (8)..(8)
<223> OTHER INFORMATION: D-Glu

<400> SEQUENCE: 65

Phe Lys Phe Glu Phe Lys Phe Glu Gly Gly Ala Ala Tyr Ser Ile Ile
1               5                   10                  15

Asn Phe Glu Lys Leu
            20

<210> SEQ ID NO 66
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 66

Ile Ser Gln Ala Val His Ala Ala His Ala Glu Ile Asn Glu Ala Gly
1               5                   10                  15

Arg Ser Gly Ser Gly Phe Lys Phe Glu Phe Lys Phe Glu
            20                  25
```

```
<210> SEQ ID NO 67
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (22)..(22)
<223> OTHER INFORMATION: D-Phe
<220> FEATURE:
<221> NAME/KEY: MISC_FEATURE
<222> LOCATION: (23)..(23)
<223> OTHER INFORMATION: D-Lys
<220> FEATURE:
<221> NAME/KEY: MISC_FEATURE
<222> LOCATION: (24)..(24)
<223> OTHER INFORMATION: D-Phe
<220> FEATURE:
<221> NAME/KEY: MISC_FEATURE
<222> LOCATION: (25)..(25)
<223> OTHER INFORMATION: D-Glu
<220> FEATURE:
<221> NAME/KEY: MISC_FEATURE
<222> LOCATION: (26)..(26)
<223> OTHER INFORMATION: D-Phe
<220> FEATURE:
<221> NAME/KEY: MISC_FEATURE
<222> LOCATION: (27)..(27)
<223> OTHER INFORMATION: D-Lys
<220> FEATURE:
<221> NAME/KEY: MISC_FEATURE
<222> LOCATION: (28)..(28)
<223> OTHER INFORMATION: D-Phe
<220> FEATURE:
<221> NAME/KEY: MISC_FEATURE
<222> LOCATION: (29)..(29)
<223> OTHER INFORMATION: D-Glu

<400> SEQUENCE: 67

Ile Ser Gln Ala Val His Ala Ala His Ala Glu Ile Asn Glu Ala Gly
1               5                   10                  15

Arg Ser Gly Ser Gly Phe Lys Phe Glu Phe Lys Phe Glu
            20                  25
```

METHODS AND COMPOSITIONS RELATED TO IMMUNOGENIC FIBRILS

This application claims priority to U.S. Provisional Patent Application Ser. No. 62/055,281 (expired), filed Sep. 25, 2014. This application claims priority to and is a continuation-in-part of U.S. application Ser. No. 13/510,863 (now U.S. Pat. No. 9,241,987), filed Jul. 18, 2013, which is a national phase application under 35 U.S.C. §371 of International Application No. PCT/US2010/57480 (expired) filed Nov. 19, 2010, which claims priority to U.S. Provisional Patent Application Ser. No. 61/263,213 (expired), filed Nov. 20, 2009, all of which are incorporated herein by reference in their entirety.

BACKGROUND OF THE INVENTION

I. Field of the Invention

Embodiments of this invention are directed generally to biology, medicine, and immunology. Certain aspects are directed to immunogenic fibrils and their use in inducing an immune response.

II. Background

The development of vaccines and other immunotherapies has been challenged by imprecise antigen display and the use of heterogeneous immune adjuvants whose mechanisms of action are complex and incompletely understood. Synthetic peptides are useful as antigens because their precise chemical definition allows one to specify the exact epitopes against which an immune response is to be raised. However, peptides are poorly immunogenic by themselves and require co-administration with strong adjuvants, a process that sacrifices the chemical definition that peptides possess initially and complicates their development and regulatory approval Lambrecht et al., 2009; Marrack et al., 2009; Purcell et al., 2007). Although several adjuvants have been investigated for peptide immunotherapies to date, current strategies such as particulates (Marrack et al., 2009; Wendorf et al., 2006), oil emulsions (Daftarian et al., 2006), toll-like receptor ligands (Ishii and Akira, 2007), ISCOMs (Maraskovsky et al., 2009), and other biologically sourced materials (McSorley et al., 2002; Sun et al., 2009) utilize chemically or structurally heterogeneous materials, making characterization and mechanistic understanding challenging. This situation has motivated the pursuit of self-adjuvanting or adjuvant-free systems (Bettahi et al., 2009; Cao et al., 2008; Toth et al., 2008).

There remains a need for additional immunogenic compositions to induce immune responses for treating microbial infection and other pathogenic conditions.

SUMMARY OF THE INVENTION

Strong antibody responses have been observed in mice without the co-administration of any additional adjuvant by non-covalently assembling a T and B cell epitope peptide into nanofibers using a short C-terminal peptide extension. It was discovered that self-assembling peptides are useful as chemically defined adjuvants. In physiological conditions, these peptides self-assembled into long, unbranched fibrils that displayed the epitope on their surfaces. IgG1, IgG2a, and IgG3 were raised against epitope-bearing fibrils in levels similar to the epitope peptide delivered in complete Freund's adjuvant (CFA), and IgM production was even greater for the self-assembled epitope. This response was dependent on self-assembly, and the self-assembling sequence was not immunogenic by itself, even when delivered in CFA.

Certain embodiments are directed to immunogenic compositions comprising a peptide fibril coupled to a plurality of antigens. In certain aspects, the peptide fibril comprises a plurality of self-assembling peptides. The peptide fibril can have a length of at least 0.25, 0.5, 1, 10, 50 to 10, 25, 50, 100 µm, including all values and ranges there between. In certain embodiments, the peptide fibril formed by the self-assembling peptides may have a length of about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 µm or nm (or any range or value derivable therein).

In certain aspects, the peptide fibril has a molecular weight of at least 1,000, 5,000, 10,000, 100,000 da to $1\times10^6$, $1\times10^7$, $7\times10^8$ da, including all values and ranges there between. In other aspects the self-assembling peptides form a beta-sheet rich fibril.

In further aspects, the self-assembling peptide comprises an amino acid sequence of FKFEFKFE (SEQ ID NO: 25); QQKFQFQFEQQ (SEQ ID NO:1); KFQFQFE (SEQ ID NO:2); QQRFQFQFEQQ (SEQ ID NO:3); QQRFQWQFEQQ (SEQ ID NO:4); FEFEFKFKFEFEFKFK (SEQ ID NO:5); QQRFEWEFEQQ (SEQ ID NO:6); QQXFXWXFQQQ (SEQ ID NO:7) (Where X denotes ornithine); FKFEFKFEFKFE (SEQ ID NO:8); FKFQFKFQFKFQ (SEQ ID NO:9); AEAKAEAKAEAKAEAK (SEQ ID NO:10); AEAEAKAKAEAEAKAK (SEQ ID NO:11); AEAEAEAEAKAKAKAK (SEQ ID NO:12); RADARADARADARADA (SEQ ID NO:13); RARADADARARADADA (SEQ ID NO:14); SGRGYBLGGQGAGAAAAAGGAGQGGYGGLGSQG (SEQ ID NO:15); EWEXEXEXEX (SEQ ID NO:16) (Where X=V, A, S, or P); WKXKXKXKXK (SEQ ID NO:17) (Where X=V, A, S, or P); KWKVKVKVKVKVKVK (SEQ ID NO:18); LLLLLKKKKKKKKLLLL (SEQ ID NO:19; VKVKVKVKVDPPTKVKVKVKV (SEQ ID NO:20; VKVKVKVKVDPPTKVKTKVKV (SEQ ID NO:21; KVKVKVKVKDPPPSVKVKVKVK (SEQ ID NO:22; or VKVKVKVKVDPPPSKVKVKVKV (SEQ ID NO:23); VKVKVKTKVDPPTKVKTKVKV (SEQ ID NO:24).

In certain aspects, the self-assembling peptide is 6, 7, 8, 9, 10, 11, 12, 13, 14, 15 to 15, 20, 25, 30, 35, 40 amino acids in length, including all values and ranges there between. In certain aspects, more than one self-assembling peptide is present in a peptide fibril. In certain aspects the self-assembling peptides comprise an immunogenic peptide or an antigen. In certain aspects the antigen(s) are polypeptides. In a further aspect the polypeptides are covalently coupled to the peptide fibril. In still a further aspect the polypeptides are covalently coupled to the peptide fibril via a cutinase polypeptide. In certain aspects, the polypeptides are covalently coupled to the peptide fibril via a SGSG (SEQ ID NO: 61) linker or a GGAAY (SEQ ID NO: 60) linker. In further embodiments, the linker may be at least, at most or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids (or any range or value derivable therein).

In further aspects, the amino acid sequence has at least, at most or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 D-amino acids (or any range or value derivable therein). In additional aspects, D-amino acids may be employed in at least, at most, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any range or value derivable therein) of any peptide, the amino acid sequence in the self-assembly peptide, or the whole immunogenic composition. In certain aspects the self-assembling peptide is composed of D amino acids.

In a further aspect, the antigen is covalently coupled to the self-assembling peptide. In a further aspect, the antigen is covalently coupled to the N and/or C terminus of the self-assembling peptide. In still further aspects, the antigen is covalently coupled to the carboxy terminus of the self-assembling peptide. In certain aspects the ratio of antigen to self-assembling peptide is 1:1000, 1:100:1:10, or 1:1, including all values and ranges there between. Antigens can be microbial antigens, such as viral, fungal, or bacterial; or therapeutic antigens such as antigens associated with cancerous cells or growths, or autoimmune disorders. In certain aspects, the antigens are peptides, lipids, carbohydrates, or other immunogenic molecules. In a further aspect, the peptides are 5, 10, 15, 20 to 15, 20, 30, 40 amino acids in length, including all values and ranges there between. The antigens can be T cell and/or B cell epitopes. In particular embodiments, the antigen may be an OVA epitope of ISQAVHAAHAEINEAGR (SEQ ID NO: 26) or a SIN epitope of SIINFEKL (SEQ ID NO: 59).

Further embodiments include self-assembling antigens comprising an antigen coupled to a fibril-forming peptide.

Certain embodiments are directed to methods of inducing an immune response comprising administering an antigenic fibril, comprising a self-assembling peptide coupled to an antigen, in an amount sufficient to induce an immune response.

Further embodiments are directed to methods of treating a subject having or at risk of developing a microbial infection, cancer, or other condition that can be treated by inducing an immune response comprising administering to the subject an effective amount of a composition described herein.

Methods may involve administering to the patient or subject at least or at most 1, 2, 3, 4, 5, 6, 7, 8, 9, 10 or more doses of a pharmaceutical composition or a composition described herein. A dose may be a composition comprising about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or µg/ml or micrograms/ml or mM or µM (or any range derivable therein) of each compound or the total amount of a combination of compounds or the compositions.

As used herein, the term "antigen" is a molecule capable of being bound by an antibody or T-cell receptor. An antigen is additionally capable of inducing a humoral immune response and/or cellular immune response leading to the production of B- and/or T-lymphocytes. The structural aspect of an antigen that gives rise to a biological response is referred to herein as an "antigenic determinant." B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant need not be a contiguous sequence or segment of protein and may include various sequences that are not immediately adjacent to one another.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figures 1A, 1B:
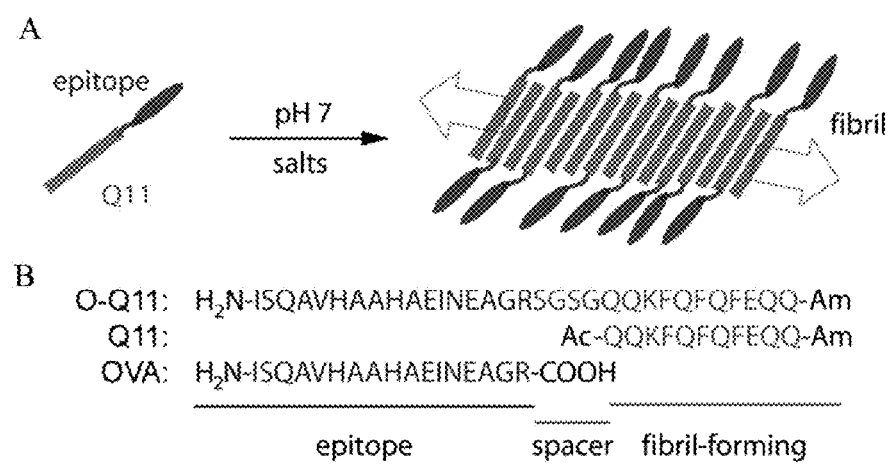
FIGS. 1A-1B Schematic (A) and sequences (B) of epitope-bearing self-assembling peptides (SEQ ID NO: 28; SEQ ID NO: 1; SEQ ID NO: 26). The Q11 domain assembles into fibrillar aggregates, displaying the epitope sequence at the end of a flexible spacer.

The development of vaccines and other immunotherapies has been challenged by imprecise antigen display and the use of heterogeneous immune adjuvants whose mechanisms of action are complex and incompletely understood. Synthetic peptides are useful as antigens because their precise chemical definition allows one to specify the exact epitopes against which an immune response is to be raised. However, peptides are poorly immunogenic by themselves and require co-administration with strong adjuvants, a process that sacrifices the chemical definition that peptides possess initially and complicates their development and regulatory approval (Lambrecht et al., 2009; Marrack et al., 2009; Purcell et al., 2007). Although several adjuvants have been investigated for peptide immunotherapies to date, current strategies such as particulates (Marrack et al., 2009; Wendorf et al., 2006), oil emulsions (Daftarian et al., 2006), toll-like receptor ligands (Ishii and Akira, 2007), ISCOMs (Maraskovsky et al., 2009), and other biologically sourced materials (McSorley et al., 2002; Sun et al., 2009) utilize chemically or structurally heterogeneous materials, making characterization and mechanistic understanding challenging. This situation has motivated the pursuit of self-adjuvanting or adjuvant-free systems (Bettahi et al., 2009; Cao et al., 2008; Toth et al., 2008).

A broad goal in the field of biomaterials is to produce synthetic scaffolds capable of presenting multiple cell-interactive components in spatially resolved networks (Lutolf and Hubbell, 2005; Place et al., 2009). To accomplish this, supramolecular self-assembly is rapidly becoming a synthetic method of choice (Silva et al., 2004; Jung et al., 2009; Collier, 2008). One strategy that has received attention recently is based on fibrillized peptides, peptidomimetics, and peptide derivatives, which are being explored for a variety of biomedical and biotechnological applications, most notably as scaffolds for regenerative medicine (Davis et al., 2005; Tysseling-Mattiace, 2008) and defined matrices for cell culture (Genove et al., 2005; Horii et al., 2007). In these applications, self-assembled materials provide several advantages, including multifunctionality, multivalency, synthetic definition, molecular specificity, and control over the nanoscale positioning of ligands and other biomolecular features (Collier, 2008). Self-assembled, multi-component matrices for cell culture using a short fibrillizing peptide, Q11 (Ac-QQKFQFQFEQQ-Am) (SEQ ID NO:1) have been described (Jung et al., 2009; Collier, 2008; Collier and Messersmith, 2003; Jung et al., 2008). This peptide, like other previously reported short fibrillizing peptides (Horii et al., 2007; Holmes et al., 2000; Aggeli et al., 1997; Gras et al., 2008), β-hairpins (Schneider et al., 2002), peptide-amphiphiles (Tysseling-Mattiace, 2008; Hartgerink et al., 2001), and peptide derivatives (Zhou et al., 2009), self-assembles in salt-containing aqueous environments to form networks of β-sheet-rich nanofibers. It is also capable of displaying functional amino acid sequences or chemical groups on the surface of its self-assembled fibers. For example, adding cell-binding amino acid sequences to the N-terminus of Q11 leads to self-assembled fibrils that functionally present the cell-binding peptides on their surfaces (Jung et al., 2009). Q11 with an N-terminal cysteine and a C-terminal thioester can undergo native chemical ligation after assembly, which can be used to stiffen the fibrillar network (Jung et al., 2008). These peptides can also be mixed to display precise combinations of different ligands (Jung et al., 2009).

During initial development as scaffolds for regenerative medicine, Q11 and other self-assembling peptide-based materials have been found to be minimally immunogenic. In previous work, Q11 and Q11 with N-terminal cell-binding RGDS sequences elicited little to no antibody responses in mice (Jung et al., 2009). Negligible tissue responses were also observed for β-sheet fibrillizing RAD16-II peptide assemblies injected within rat (Hsieh et al., 2006) or mouse (Davis et al., 2005) myocardium. Low antibody titers have also been reported in rabbits and goats for RAD16 peptides (Holmes et al., 2000). One study observed an inflammatory response to RAD16 peptides in rats, but the causes were not known (Dubois et al., 2008). The minimal immunogenicity of these materials observed to date is clearly advantageous for applications in regenerative medicine, but previous work has focused largely on amino acid sequences that are already found in endogenous proteins, for example the RGDS cell-binding sequence from fibronectin (Jung et al., 2009; Guler et al., 2006). Because of this, strong epitopes have effectively been avoided. In the present work, it was sought to determine the extent to which the previously observed low immunogenicity also applied to peptide sequences containing stronger epitopes. The results show a surprisingly robust antibody response generated against a self-assembled B and T cell epitope, indicating that self-assembled peptides can serve as powerful chemically defined adjuvants.

I. Self-Assembling Peptides

Certain aspects of the invention include self-assembling peptides. As used herein, the term "self-assembling peptide" refers to peptides that are able to spontaneously associate and form stable structures. In one embodiment, a self-assembling peptide comprises an amino acid sequence of FKFEFKFE (SEQ ID NO: 25); (FKFE)n, n=1-50 (SEQ ID NO: 62); QQKFQFQFEQQ (SEQ ID NO: 1); KFQFQFE (SEQ ID NO: 2); QQRFQFQFEQQ (SEQ ID NO: 3); QQRFQWQFEQQ (SEQ ID NO: 4); FEFEFKFK-FEFEFKFK (SEQ ID NO: 5); QQRFEWEFEQQ (SEQ ID NO: 6); QQXFXWXFQQQ (Where X denotes ornithine) (SEQ ID NO: 7); FKFEFKFEFKFE (SEQ ID NO: 8); FKFQFKFQFKFQ (SEQ ID NO: 9); AEAKAEAKAEA-KAEAK (SEQ ID NO: 10); AEAEAKAKAEAEAKAK (SEQ ID NO: 11); AEAEAEAEAKAKAKAK (SEQ ID NO: 12); RADARADARADARADA (SEQ ID NO: 13); RARADADARARADADA (SEQ ID NO: 14); SGRGY-BLGGQGAGAAAAAGGAGQGGYGGLGSQG (SEQ ID NO: 15); EWEXEXEXEX (Where X=V, A, S, or P) (SEQ ID NO: 16); WKXKXKXKXK (Where X=V, A, S, or P) (SEQ ID NO: 17); KWKVKVKVKVKVKVK (SEQ ID NO: 18); LLLLKKKKKKKKLLLL (SEQ ID NO: 19); VKVKVKVKVDPPTKVKVKVKV (SEQ ID NO: 20); VKVKVKVKVDPPTKVKTKVKV (SEQ ID NO: 21); KVKVKVKVKDPPSVKVKVKVK (SEQ ID NO: 22); VKVKVKVKVDPPSKVKVKVKV (SEQ ID NO: 23); VKVKVKTKVDPPTKVKTKVKV (SEQ ID NO: 24) or conservatively modified variants thereof.

In certain embodiments, the peptides may be 50 residues or less. The overall length may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues. Ranges of peptide length of 4-50 residues, 7-50 residues, 4-25 residues 7-25, residues, 4-20 residues, 7-20 residues, and 3-15 residues, and 7-15 residues are contemplated.

In certain embodiments, at least or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more (or any range or value derivable therein) of the amino acids in the amino acid sequence in a self-assembling peptide are D amino acids. In further embodiments, all of the amino acids in the amino acid sequence are D amino acids.

Self-assembling peptides may further comprise other compounds, for example, immunogenic peptides.

Certain peptides that comprise of alternating hydrophilic and hydrophobic amino acids self-assemble to form an exceedingly stable beta-sheet macroscopic scaffold (U.S. Pat. Nos. 5,955,343 and 5,670,483, each of which is incorporated herein by reference).

Many self-complementary peptides have identical compositions and length; such as EAK16, KAE16, RAD16, RAE16, and KAD16; have been analyzed previously (Table 1).

TABLE 1

Representative Self-Assembling peptides

| Name | Sequence (n-->c) | SEQ ID NO: | Modulus | Structure |
|---|---|---|---|---|
| RADA16-I | n-RADARADARADARADA-c | 29 | I | β |
| RGDA16-I | n-RADARGDARADARGDA-c | 30 | I | r.c |
| RADA8-I | n-RADARADA-c | 31 | I | r.c. |
| RAD16-II | n-RARADADARARADADA-c | 32 | II | β |
| RAD8-II | n-RARADADA-c | 33 | II | r.c. |
| EAKA16-I | n-AEAKAEAKAEAKAEAK-c | 34 | I | β |
| EAKA8-I | n-AEAKAEAK-c | 35 | I | r.c. |
| RAEA16-I | n-RAEARAEARAEARAEA-c | 36 | I | β |
| RAEA8-I | n-RAEARAEA-c | 37 | I | r.c. |
| KADA16-I | n-KADAKADAKADAKADA-c | 38 | I | β |
| KADA8-I | n-KADAKADA-c | 39 | I | r.c. |
| EAH16-II | n-AEAEAHAHAEAEAHAHA-c | 40 | II | β |
| EAH8-II | n-AEAEAHAHA-c | 41 | II | r.c. |
| EFK16-II | n-FEFEFKFKFEFEFKFK-c | 42 | II | β |
| EFK8-II | n-FEFKFEFK-c | 43 | I | β |

TABLE 1-continued

Representative Self-Assembling peptides

| Name | Sequence (n-->c) | SEQ ID NO: | Modulus | Structure |
|---|---|---|---|---|
| ELK16-II | n-LELELKLKLELELKLK-c | 44 | II | β |
| ELK8-II | n-LELELKLK-c | 45 | II | r.c. |
| EAK16-II | n-AEAEAKAKAEAEAKAK-c | 46 | II | β |
| EAK12 | n-AEAEAEAEAKAK-c | 47 | IV/II | α/β |
| EAK8-II | n-AEAEAKAK-c | 48 | II | r.c. |
| KAE16-IV | n-KAKAKAKAEAEAEAEA-c | 49 | IV | β |
| EAK16-IV | n-AEAEAEAEAKAKAKAK-c | 50 | IV | β |
| RAD16-IV | n-RARARARADADADADA-c | 51 | IV | β |
| DAR16-IV | n-ADADADADARARARAR-c | 52 | IV | α/β |
| DAR16-IV* | n-DADADADARARARARA-c | 53 | IV | α/β |
| DAR32-IV | n-(ADADADADARARARAR)-c | 52 | IV | α/β |
| EHK16 | n-HEHEHKHKHEHEHKHK-c | 54 | N/A | r.c. |
| EKH8-I | n-HEHEHKHK-c | 55 | N/A | r.c. |
| VE20* | n-VEVEVEVEVEVEVEVEVE-c | 56 | N/A | β |
| RF20* | n-RFRFRFRFRFRFRFRFRFRF-c | 57 | N/A | β |

β denotes beta-sheet;
α denotes alpha-helix;
r.c. denotes random coil;
N/A denotes not applicable.
*Both VE20 and RF20 form a beta-sheet when they are incubated in a solution containing NaCl; however, they do not self-assemble to form macroscopic scaffolds.

The peptides described herein can be chemically synthesized using standard chemical synthesis techniques. In some embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are well known to those of skill in the art and are described, for example, by Barany and Merrifield (1963) Solid-Phase Peptide Synthesis; pp. 3-284 in The Peptides: Analysis, Synthesis, Biology. Vol. 2: Special Methods in Peptide Synthesis, Part A.; Merrifield et al. (1963) J. Am. Chem. Soc., 85: 2149-2156, and Stewart et al. (1984) Solid Phase Peptide Synthesis, 2nd ed. Pierce Chem. Co., Rockford, Ill.

II. Antigens

The term "antigen" as used herein refers to a molecule against which a subject can initiate a humoral and/or cellular immune response. Antigens can be any type of biologic molecule including, for example, simple intermediary metabolites, sugars, lipids, and hormones as well as macromolecules such as complex carbohydrates, phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, and other miscellaneous antigens. In certain compositions and methods of the invention, the antigen is a peptide. In particular embodiments, the antigen may be an OVA epitope of ISQAVHAAHAEINEAGR (SEQ ID NO: 26) or a SIN epitope of SIINFEKL (SEQ ID NO: 59).

Viral Antigens. Examples of viral antigens include, but are not limited to, retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B. and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS 1, NS 1, NS 1-NS2A, 80% E, and other Japanese encephalitis viral antigen components; rabies viral antigens such as rabies glycoprotein, rabies nucleoprotein and other rabies viral antigen components. See Fundamental Virology, Second Edition, e's. Fields, B. N. and Knipe, D. M. (Raven Press, New York, 1991) for additional examples of viral antigens.

Bacterial Antigens. Bacterial antigens which can be used in the compositions and methods of the invention include, but are not limited to, pertussis bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diphtheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; *Hemophilus influenza* bacterial antigens such as capsular polysaccharides and other *Hemophilus influenza* bacterial antigen components; anthrax bacterial antigens such as anthrax protective antigen and other anthrax bacterial antigen components; rickettsiae bacterial antigens such as romps and other rickettsiae bacterial antigen component. Also included with the bacterial antigens described herein are any other bacterial, mycobacterial, mycoplasmal, rickettsial, or chlamydial antigens.

Fungal Antigens. Fungal antigens which can be used in the compositions and methods of the invention include, but are not limited to, Candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Parasite Antigens. Examples of protozoa and other parasitic antigens include, but are not limited to, *plasmodium falciparum* antigens such as merozoite surface antigens, sporozoite surface antigens, circumsporozoite antigens, gametocyte/gamete surface antigens, blood-stage antigen pf 1 55/RESA and other plasmodial antigen components; toxoplasma antigens such as SAG-1, p30 and other toxoplasma antigen components; schistosomae antigens such as glutathione-S-transferase, paramyosin, and other schistosomal antigen components; *leishmania major* and other leishmaniae antigens such as gp63, lipophosphoglycan and its associated protein and other leishmanial antigen components; and *trypanosoma cruzi* antigens such as the 75-77 kDa antigen, the 56 kDa antigen and other trypanosomal antigen components.

Tumor Antigens. Tumor antigens which can be used in the compositions and methods of the invention include, but are not limited to, telomerase components; multidrug resistance proteins such as P-glycoprotein; MAGE-1, alpha fetoprotein, carcinoembryonic antigen, mutant p53, immunoglobulins of B-cell derived malignancies, fusion polypeptides expressed from genes that have been juxtaposed by chromosomal translocations, human chorionic gonadotrpin, calcitonin, tyrosinase, papillomavirus antigens, gangliosides or other carbohydrate-containing components of melanoma or other tumor cells. It is contemplated by the invention that antigens from any type of tumor cell can be used in the compositions and methods described herein.

Antigens Relating to Autoimmunity. Antigens involved in autoimmune diseases, allergy, and graft rejection can be used in the compositions and methods of the invention. For example, an antigen involved in any one or more of the following autoimmune diseases or disorders can be used in certain aspects: diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves opthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy include pollen antigens such as Japanese cedar pollen antigens, ragweed pollen antigens, rye grass pollen antigens, animal derived antigens such as dust mite antigens and feline antigens, histocompatiblity antigens, and penicillin and other therapeutic drugs. Examples of antigens involved in graft rejection include antigenic components of the graft to be transplanted into the graft recipient such as heart, lung, liver, pancreas, kidney, and neural graft components. An antigen can also be an altered peptide ligand useful in treating an autoimmune disease.

Examples of miscellaneous antigens which can be can be used in the compositions and methods of the invention include endogenous hormones such as luteinizing hormone, follicular stimulating hormone, testosterone, growth hormone, prolactin, and other hormones, drugs of addiction such as cocaine and heroin, and idiotypic fragments of antigen receptors such as Fab-containing portions of an anti-leptin receptor antibody.

III. Pharmaceutical Compositions

The present invention includes methods for preventing or ameliorating microbial infections. As such, the invention contemplates vaccines and therapeutics for use in active immunization of subjects. Immunogenic compositions can include a peptide fibril coupled to a plurality of antigens, "fibril complex."

The preparation of vaccines that contain polypeptide or peptide sequence(s) as active ingredients is generally well understood in the art, as exemplified by U.S. Pat. Nos. 4,608,251; 4,601,903; 4,599,231; 4,599,230; 4,596,792; and 4,578,770, all of which are incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines and therapeutics may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The compositions described herein may be formulated into a pharmaceutical composition as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Typically, compositions are administered in a manner compatible with the dosage formulation, and in such amount as will be therapeutically effective and immunogenic. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection and the like. The dosage of the vaccine will depend on the route of administration and will vary according to the size and health of the subject.

The compositions and related methods, particularly administration of a peptide fibril/antigen complex may also be used in combination with the administration of traditional therapies. These include, but are not limited to, the administration of antibiotics such as streptomycin, ciprofloxacin, doxycycline, gentamycin, chloramphenicol, trimethoprim, sulfamethoxazole, ampicillin, tetracycline or various combinations of antibiotics.

In one aspect, it is contemplated that a peptide fibril/antigen vaccine and/or therapy is used in conjunction with antibacterial treatment. Alternatively, the therapy may precede or follow the other agent treatment by intervals ranging from minutes to weeks. In embodiments where the other agents and/or a proteins is administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations may be employed, for example antibiotic therapy is "A" and the immunogenic composition is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the immunogenic compositions of interest to a patient/subject will follow general protocols for the administration of such immunogenic compositions, taking into account the toxicity, if any. It is expected that the treatment cycles would be repeated as necessary. It also is contemplated that various standard therapies, such as hydration, may be applied in combination with the described therapy.

In some embodiments, pharmaceutical compositions are administered to a subject. Different aspects may involve administering an effective amount of a composition to a subject. In some embodiments, immunogenic compositions may be administered to the patient to protect against infection by one or more microbial pathogens. Additionally, such pharmaceutical compositions can be administered in combination with an antibiotic or other known anti-microbial therapy. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-cancer agents, can also be incorporated into the compositions.

In addition to the pharmaceutical compositions that may be formulated for parenteral administration, such as those for intravenous or intramuscular injection, other pharmaceutically acceptable forms include, e.g., tablets or other solids for oral administration; time release capsules; and any other form currently used, including creams, lotions, mouthwashes, inhalants and the like.

The active pharmaceutical compositions in certain embodiments can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the pharmaceutical compositions as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Administration of the compositions according to the present invention will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion, (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

IV. Peptide Structures

Certain aspects may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

Because the L-amino acids is the natural configuration, the peptide nanofibers containing D amino acids are markedly different in structure from naturally-occurring peptides. In certain embodiments, there are provided peptides that comprise one or more D amino acids. In further embodiments, D-amino acids may be used in at least or about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any range or value derivable therein) of the peptide. In some embodiments, the D-amino acid peptide nanofibers may surprisingly elicit stronger antibody responses compared to L amino acid peptide nanofibers with the same amino acid sequence.

The use of D-amino acids in vaccine development may be unexpected because most vaccine adjuvants have used only L-amino acids. Most vaccine adjuvants are limited in their ability to induce strong immune responses without associated toxicity and there is an ever-growing need for effective and safe adjuvants (O'Hagan, et al., 2009). Self-assembling peptides that form β-sheet rich nanofibers have been reported to elicit strong immune responses in mice when linked to peptide or protein antigens (Rudra, et al., 2010; Hudalla, et al., 2013; Chesson, et al., 2013). This adjuvanting capability was not restricted to the primary sequence of the self-assembling domain, position of the epitope, linker sequence, mouse strains, or, the route of immunization (Rudra, et al., 2012; Rudra, et al., 2012; Huang, et al., 2012). Immunization with peptide nanofibers bearing disease-relevant epitopes has been shown to be protective in murine models of malaria and cancer (Rudra, et al., 2012; Huang, et al., 2012). Interestingly, strong immune responses have not been detected against self-assembling peptides even when co-administered with strong exogenous adjuvants, which makes them ideal for applications in vaccine development and immunotherapy (Rudra, et al., 2010; Rudra, et al., 2012). While both L- and D- amino acids are chemically possible, naturally occurring proteins utilize only the L-form. Therefore it is not surprising that most self-assembling peptides designed to date have utilized naturally occurring L amino acids (Bowerman, et al., 2012; Collier, et al., 2010; Maude, et al., 2013).

In further embodiments, peptides modified for in vivo use by the addition, at the amino- and/or carboxyl-terminal ends, of a blocking agent to facilitate survival of the peptide in vivo may be contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino and/or carboxyl terminal residues.

Because of their relatively small size, the peptides in certain aspects can be synthesized in solution or on a solid support in accordance with conventional techniques. Various automatic synthesizers are commercially available and can be used in accordance with known protocols. See, for example, Stewart and Young, 1984; Tam et al., 1983; Merrifield, 1986; Barany and Merrifield, 1979, each incorporated herein by reference. Short peptide sequences, usually from about 6 up to about 35 to 50 amino acids, can be readily synthesized by such methods. Alternatively, recombinant DNA technology may be employed wherein a nucleotide sequence which encodes a peptide is inserted into an expression vector, transformed or transfected into an appropriate host cell, and cultivated under conditions suitable for expression.

V. Linkers

The antigen or the self-assembling peptide can be truncated and replaced by short linkers or they can be conjugated by linkers. In some embodiments, the antigen or the polypeptide include one or more peptide linkers. For example, a linker consists of from 2 to 25 amino acids. Usually, it is from 2 to 15 amino acids in length, although in certain circumstances, it can be only one, such as a single glycine residue.

In one embodiment, a nucleic acid molecule, in which polynucleotide encoding the self-assembling peptide is genetically fused with polynucleotide encoding the antigen, is expressed in a host cell so that the first attachment site and the second attachment site are linked through a peptide bond. In this case, the polypeptide and the antigen are linked through a peptide bond. Relating to this embodiment, the first attachment site and/or the second attachment site may be genetically modified from the original polypeptide or antigen. For example, the first attachment site is modified from the polypeptide so that through a linker peptide including SG, GS, SGG, GGS and SGSG (SEQ ID NO: 61), the polypeptide is conjugated with the antigen.

When the polypeptide are chemically conjugated with the antigen, the first attachment site and the second attachment site may be linked through a chemical cross-linker which is a chemical compound.

Examples of the cross-linker include, but are not limited to, SMPH, Sulfo-MBS, Sulfo-EMCS, Sulfo-GMBS, Sulfo-SIAB, Sulfo-SMPB, Sulfo-SMCC, SVSB, SIA and other cross-linkers available from the Pierce Chemical Company.

If desired, the peptides of interest may be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metallaproteinase, such as collagenase, gelatinase, or stromelysin.

Additionally, while numerous types of disulfide-bond containing linkers are known which can successfully be employed to conjugate moieties, certain linkers may be chosen over other linkers, based on differing pharmacologic characteristics and capabilities. For example, linkers that contain a disulfide bond that is sterically "hindered" are to be preferred, due to their greater stability in vivo, thus preventing release of the moiety prior to binding at the site of action.

Additionally, any other linking/coupling agents and/or mechanisms known to those of skill in the art can be used to combine to peptides, components or agents of interest, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

Cross-linking reagents may be used to form molecular bridges that tie together functional groups of two different molecules, e.g., a stabilizing and coagulating agent. However, it is contemplated that dimers or multimers of the same analog can be made or that heteromeric complexes comprised of different analogs can be created. To link two different compounds or peptides in a step-wise manner, hetero-bifunctional cross-linkers can be used that eliminate unwanted homopolymer formation.

VI. Proteinaceous Compositions

In certain embodiments, there are provided novel compositions comprising at least one proteinaceous molecule and methods for preparing and using such compositions. The proteinaceous molecules may be used for forming a β-sheet structure or nanofiber or be packaged in the structure as an active compound attached to peptide A or non-β-sheet peptides.

As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein. For convenience, the terms "protein," "polypeptide" and "peptide" may be used interchangeably herein.

In certain embodiments the size of the at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino molecule residues, and any range derivable therein.

In some aspects the size of a peptide defined in certain aspects of the present invention may comprise, but is not limited to, 5, 6, 7, 8, 9, 10, 11, 12, 13, 14, 15, 16, 17, 18, 19, 20 amino acid residues. In other aspects the size of a peptide may comprise, but is not limited to, 5, 6, 7, 8, 9, 10, 11, 12, 13, 14, 15, 16, 17, 18, 19, 20, 21, 22, 23, 24, 25, 26, 27, 28, 29, 30 amino acid residues, or any range derivable therein.

In certain embodiments, peptides less than or equal to 20 amino acids, or peptides 6-10 amino acids in length may be used.

As used herein, an "amino acid molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to those shown on Table 2 below.

TABLE 2

Modified and Unusual Amino Acids

| Abbr. | Amino Acid | Abbr. | Amino Acid |
| --- | --- | --- | --- |
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In certain embodiments the proteinaceous composition comprises at least one protein, polypeptide or peptide. In further embodiments the proteinaceous composition comprises a biocompatible protein, polypeptide or peptide. As used herein, the term "biocompatible" refers to a substance which produces no significant untoward effects when applied to, or administered to, a given cell or organism according to the methods and amounts described herein. Organisms include, but are not limited to, such untoward or undesirable effects are those such as significant toxicity or adverse immunological reactions. In particular embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compositions from natural sources, or the chemical synthesis of proteinaceous materials.

The nucleotide and protein, polypeptide and peptide sequences for various genes have been previously disclosed, and may be found at computerized databases known to those of ordinary skill in the art. One such database is the National Center for Biotechnology Information's Genbank and GenPept databases (available at www.ncbi.nlm.nih.gov/). The coding regions for these known genes may be amplified and/or expressed using the techniques disclosed herein or as would be known to those of ordinary skill in the art. Alternatively, various commercial preparations of proteins, polypeptides and peptides are known to those of skill in the art.

B. Purification or Isolation

In certain embodiments a protein or peptide or a composition comprising such a protein or peptide may be isolated or purified. Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. An example of receptor protein purification by affinity chromatography is disclosed in U.S. Pat. No. 5,206,347, the entire text of which is incorporated herein by reference. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

A peptide, polypeptide or protein that is "purified to homogeneity," as applied in certain embodiments, means that the peptide, polypeptide or protein has a level of purity where the peptide, polypeptide or protein is substantially free from other proteins and biological components. For example, a purified peptide, polypeptide or protein will often be sufficiently free of other protein components so that degradative sequencing may be performed successfully.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A particular method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

To purify a desired protein, polypeptide, or peptide a natural or recombinant composition comprising at least some specific proteins, polypeptides, or peptides may be subjected to fractionation to remove various other components from the composition. Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Another example is the purification of a specific fusion protein using a specific binding partner. Such purification methods are routine in the art. Certain aspects provide DNA sequences for the specific proteins, and any fusion protein purification method may be practiced. However, given many DNA and proteins are known, or may be identified and amplified using the methods described herein, any purification method can now be employed.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

C. Fusion Proteins

Other embodiments of protein conjugates concern fusion proteins. These molecules generally have all or a substantial portion of an antigenic peptide, linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope, to, for example, facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

In particular embodiments, the fusion proteins comprise a peptide tag attached to an antigenic protein or peptide. Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. These examples are not meant to be limiting and it is contemplated that within the scope of the present invention virtually any protein or peptide could be incorporated into a fusion protein comprising a peptide tag. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding a peptide tag to a DNA sequence encoding the second peptide or protein, followed by expression of the intact fusion protein.

VII. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Peptide Fibrils as Immune Adjuvants

A. Results

Peptide Design and Supramolecular Assembly. The peptide Q11 was previously designed as a self-assembling transglutaminase substrate (Collier and Messersmith, 2003) and was a variation on the DN1 peptide originally described by Aggeli and coworkers (Aggeli et al., 1997; Riley et al., 2009). A peptide containing a Q11 self-assembling domain was designed to include in tandem an $OVA_{323-339}$, a 17-amino acid peptide from chicken egg ovalbumin (FIG. 1). $OVA_{323-339}$ (ISQAVHAAHAEINEAGR (SEQ ID NO:26), hereafter referred to as OVA) is an $H-2^b$-restricted class II peptide containing multiple antigenic determinants, including known T and B cell epitopes (Yang and Mine, 2009). The self-assembling epitope peptide (O-Q11) was produced by solid phase synthesis and included a hydrophilic Ser-Gly-Ser-Gly spacer between the OVA and Q11 domains, with the OVA domain positioned at the N-terminus (FIG. 1B).

Figures 2A, 2B, 2C, 2D, 2E, 2F:
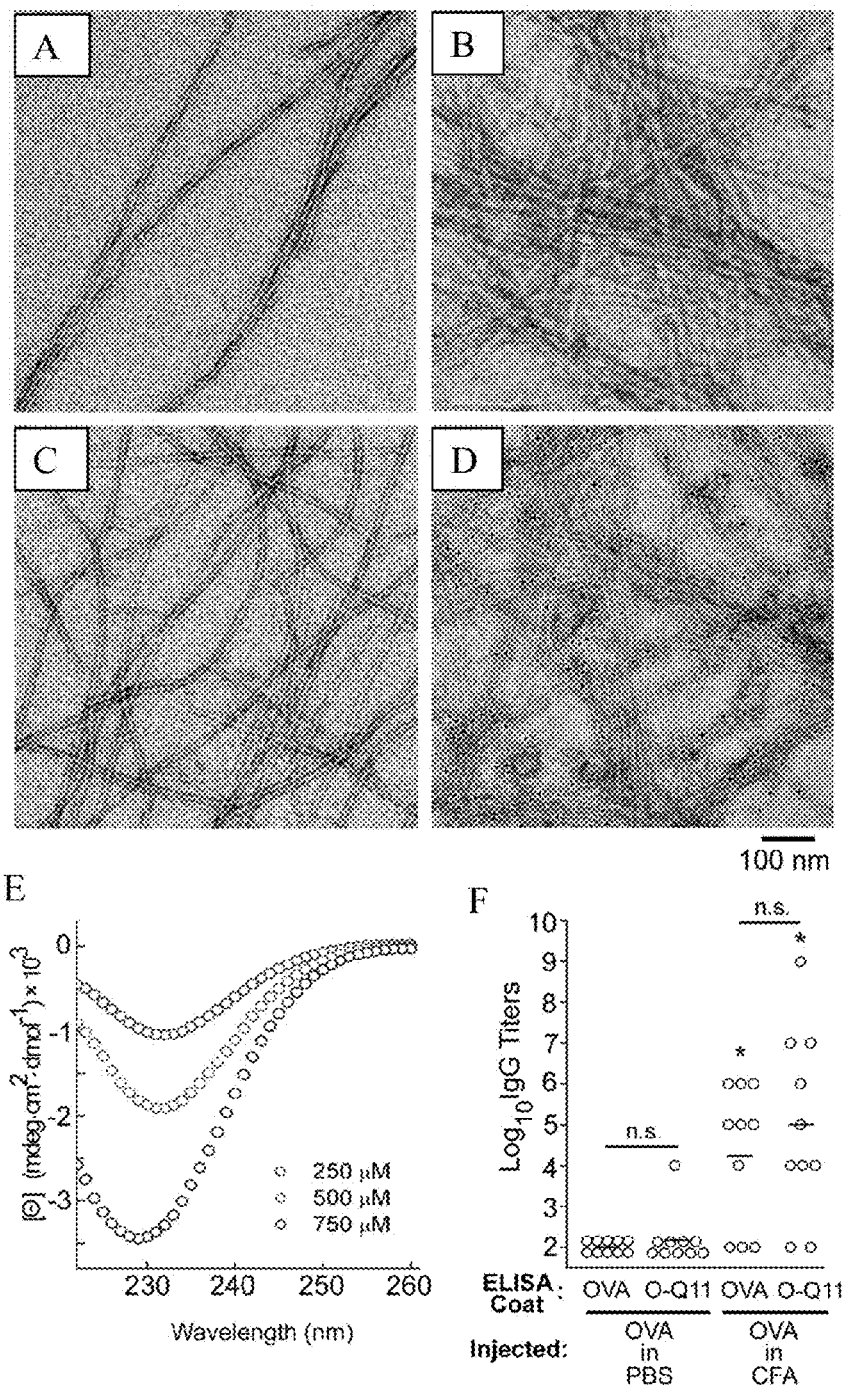
FIGS. 2A-2F Q11-based peptides self-assembled into β-sheet fibrils that displayed functional epitopes on their surfaces. Q11 (A) self-assembled into long, unbranched fibrils that did not bind streptavidin-gold (B). O-Q11 (C) also formed long, unbranched fibrils, and biotin-O-Q11 bound streptavidin-gold (D), indicating availability of the N-terminus on the fibril surface. O-Q11 possessed a predominant β-sheet structure by CD (E). OVA antisera reacted similarly to ELISA plates coated with OVA or O-Q11 (F). Each point represents one mouse's serum; bars represent the mean. *$p<0.01$ compared to OVA coat/OVA in PBS injection, by ANOVA with Tukey HSD post-hoc testing. n.s., not statistically different.

When dissolved in water at concentrations of 40 mM and lower, O-Q11 formed no visible precipitate. However, similar to Q11 and to other previously reported Q11 derivatives (Collier, 2008; Collier and Messersmith, 2003; Jung et al., 2008), it formed networks of laterally entangled fibrils when it was first dissolved in water and then added to salt-containing buffers such as phosphate-buffered saline (PBS), (FIG. 1A, FIG. 2). By TEM, O-Q11 in PBS appeared as long, unbranched fibrils with widths of about 15 nm (FIG. 2C). Although the length of these fibrils was not directly measured, the relative scarcity of fibril ends in TEM images suggested that the fibril length was on the order of microns. Circular dichroism of O-Q11 showed a single concentration-dependent minimum at 229-232 nm (FIG. 2E). This spectrum is consistent with a high degree of β-sheet or β-turn structure, and it is similar to the spectra of Q11 and mixtures of Q11 with other previously reported ligand-bearing Q11 derivatives (Jung et al., 2009; Collier and Messersmith, 2003).

Epitopes were functionally displayed on O-Q11 fibrils. The availability of the OVA epitope on the surface of O-Q11 nanofibers was confirmed by TEM and by ELISA. To label epitopes in TEM samples, an N-terminally biotinylated O-Q11 was synthesized with a single biotin tag directly adjacent to the OVA sequence. This biotinylated peptide produced fibrils that appeared morphologically similar to O-Q11 (FIG. 2D). Five-nanometer streptavidin-conjugated gold particles were then used to probe epitope availability on the fibril surface, with unmodified Q11 serving as a negative control. Biotin-O-Q11 fibrils stained strongly with streptavidin-gold, whereas Q11 samples bound negligible numbers of particles (FIG. 2B-2D), demonstrating that a significant portion of the peptides' N-termini were available on the surface of the fibrils. To confirm this finding and to quantify the availability of the entire epitope, ELISA was employed. Plates coated with OVA and O-Q11 peptides were probed with antisera from mice immunized with OVA, either with or without complete Freund's adjuvant (CFA). Antisera from CFA-adjuvanted groups showed similar titers of OVA-reactive IgG, whether measured on OVA plates or on O-Q11 plates, and both showed low backgrounds for antisera from non-adjuvanted groups (FIG. 2F). This result indicated that the OVA epitope was functionally presented on the surface of the Q11 fibrils, and that plates coated with O-Q11 fibrils produced similar signal strengths to plates coated with the non-fibrillized OVA peptide, allowing the sera of mice immunized with different peptides to be compared. Slightly higher titers were observed for the O-Q11-coated plates in both cases, but it was not statistically significant.

Figures 3A, 3B, 3C, 3D:
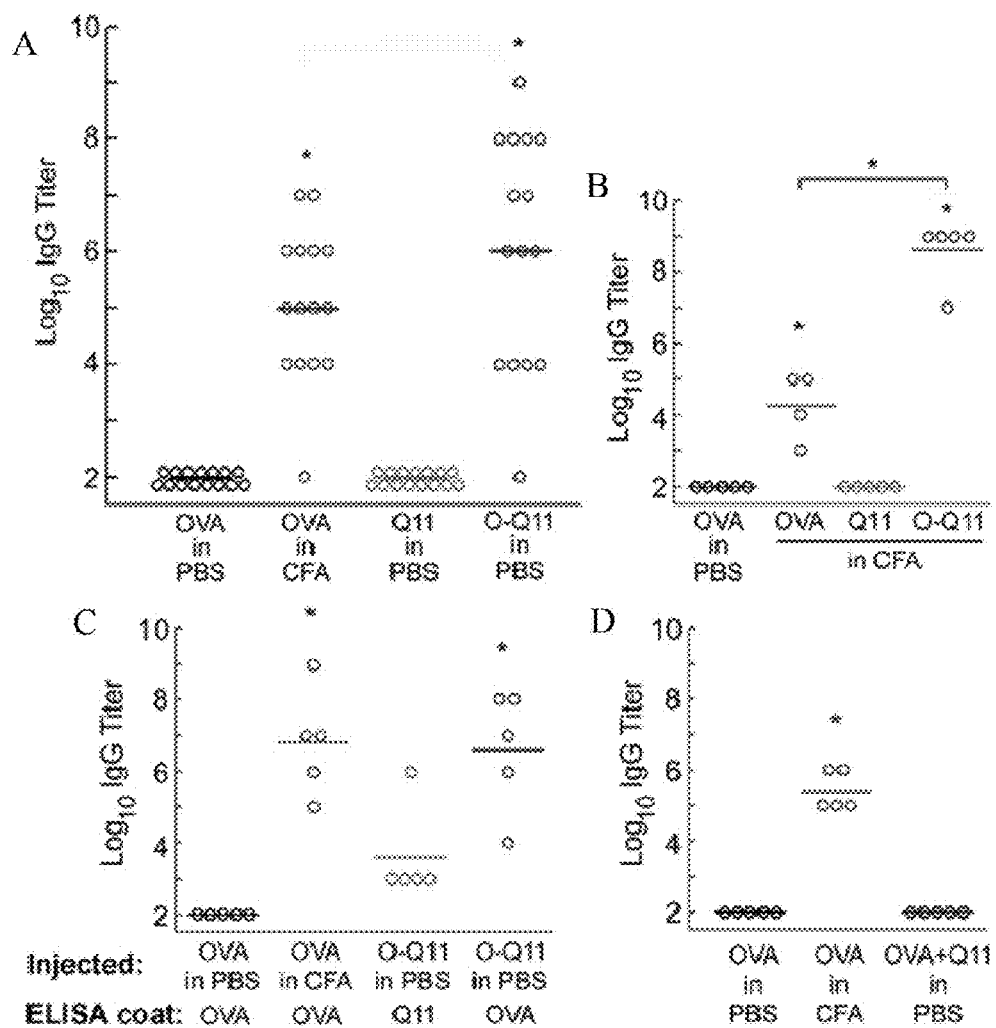
FIGS. 3A-3D Fibrillization by the Q11 domain strongly adjuvanted IgG responses to OVA. Similar titers of total IgG were raised against O-Q11 delivered in PBS and OVA delivered in CFA, whereas Q11 or OVA delivered in PBS did not elicit a response (A). Q11 was non-immunogenic even in CFA, whereas CFA increased IgG titers for O-Q11 (B). O-Q11 antisera were strongly cross-reactive to OVA-coated ELISA plates and showed a small amount of reactivity to Q11-coated plates that was not statistically significant (C). The adjuvant activity of Q11 was entirely dependent on covalent conjugation between the fibrillizing domain and epitope domain, as mixtures of Q11 and OVA did not raise any OVA-specific IgG (D). Each point represents one mouse; bars represent the mean. *$p<0.01$ by ANOVA with Tukey HSD post-hoc testing, compared with OVA in PBS, or between groups as indicated.

High IgG titers were elicited by O-Q11 without adjuvant in mice. To investigate how fibrillization affected the immunogenicity of OVA, C57BL/6 mice were immunized subcutaneously with the different peptides and boosted with additional peptide at 28 days (see methods). Serum was collected seven days after the boost, and levels of various immunoglobulins were measured. It was found that fibrillized Q11 alone did not raise any detectable IgG, whether delivered with or without CFA (FIG. 3A-3B). This result reiterated previous findings that Q11 was not immunogenic (Jung et al, 2009) and further indicated that Q11 continued to be non-immunogenic even when delivered in CFA. Also, Q11 and functionalized Q11 peptides did not induce cell death in cultures of primary human endothelial cells, indicating that the basic Q11 sequence was non-cytotoxic as well as non-immunogenic (Jung et al., 2009; Jung et al., 2008).

In surprising contrast to the immeasurably low immunogenicity of Q11, O-Q11 elicited high IgG titers without any added adjuvant (FIG. 3A). Even higher titers were produced when it was delivered in CFA (FIG. 3B). Anti-peptide IgG titers were similar between mice injected with O-Q11 in PBS and OVA peptide in CFA, indicating that the Q11 sequence itself functioned as a strong adjuvant. O-Q11 antisera also bound to OVA-coated plates, demonstrating that the epitope was conserved (FIG. 3C). O-Q11 antiserum reactivity to OVA-coated plates also excluded the possibility that the high antibody titers found in O-Q11 antisera were a measurement artifact arising from increased antigen density on fibril-coated ELISA plates. In addition, endotoxin levels were less than 0.3 EU/mL for all samples (Table 3), eliminating the possibility that inadvertent contamination caused the observed adjuvant effect. O-Q11 antisera also reacted with Q11, though at smaller, statistically insignificant levels (FIG. 3C), possibly indicating a small degree of epitope spreading to the Q11 domain.

TABLE 3

| | Purity (%) by HPLC[a] | Endotoxin (EU/mL)[a,b] | (m/z) calc'd | (m/z) found[a] |
|---|---|---|---|---|
| Q11 | 92.0-97.5% | 0.024-0.098 | 1526.7 | 1527.2-1529.4 |
| OVA$_{323-339}$ | 91.6-95% | bkgd-0.112 | 1773.9 | 1774.0-1774.3 |
| O-Q11 | 96.2-98.0% | 0.08-0.28 | 3528.8 | 3528.3-3530.1 |

[a]Ranges represent high and low values among three batches for each peptide.
[b]All are within acceptable limits [Malyala P, Singh M (2008), Endotoxin limits in formulations for preclinical research *J Pharm Sci* 97, 2041-2044].

It is contemplated that the multivalent surface display of the epitope on the fibrils was the source of Q11's strong adjuvant properties. Alternatively, if Q11 functioned as an adjuvant by activating Toll-like receptors, similarly to LPS or unmethylated CpG motifs, or if it simply slowed the diffusion of the epitope from the injection site by surrounding it with fibrils (the so-called "depot effect"), then outright conjugation of the epitope and the fibril would not be required. Additionally, if Q11 fibrils functioned in a manner similar to particulate adjuvants such as aluminum salts, whereby the adsorption and entrapment of the antigen onto and within the particle is sufficient for adjuvancy, then conjugation would also not be required. To investigate this aspect, mice were injected with unconjugated mixtures of Q11 peptide and OVA peptide. Notably, the strong antibody response generated by O-Q11 was completely abolished in the absence of covalent coupling between the Q11 fibrillizing domain and the epitope domain (FIG. 3D). No detectable IgG was observed for mixtures of OVA and Q11. This result indicated that Q11's adjuvant properties were dependent on its covalent attachment to the epitope peptide.

Figure 4:
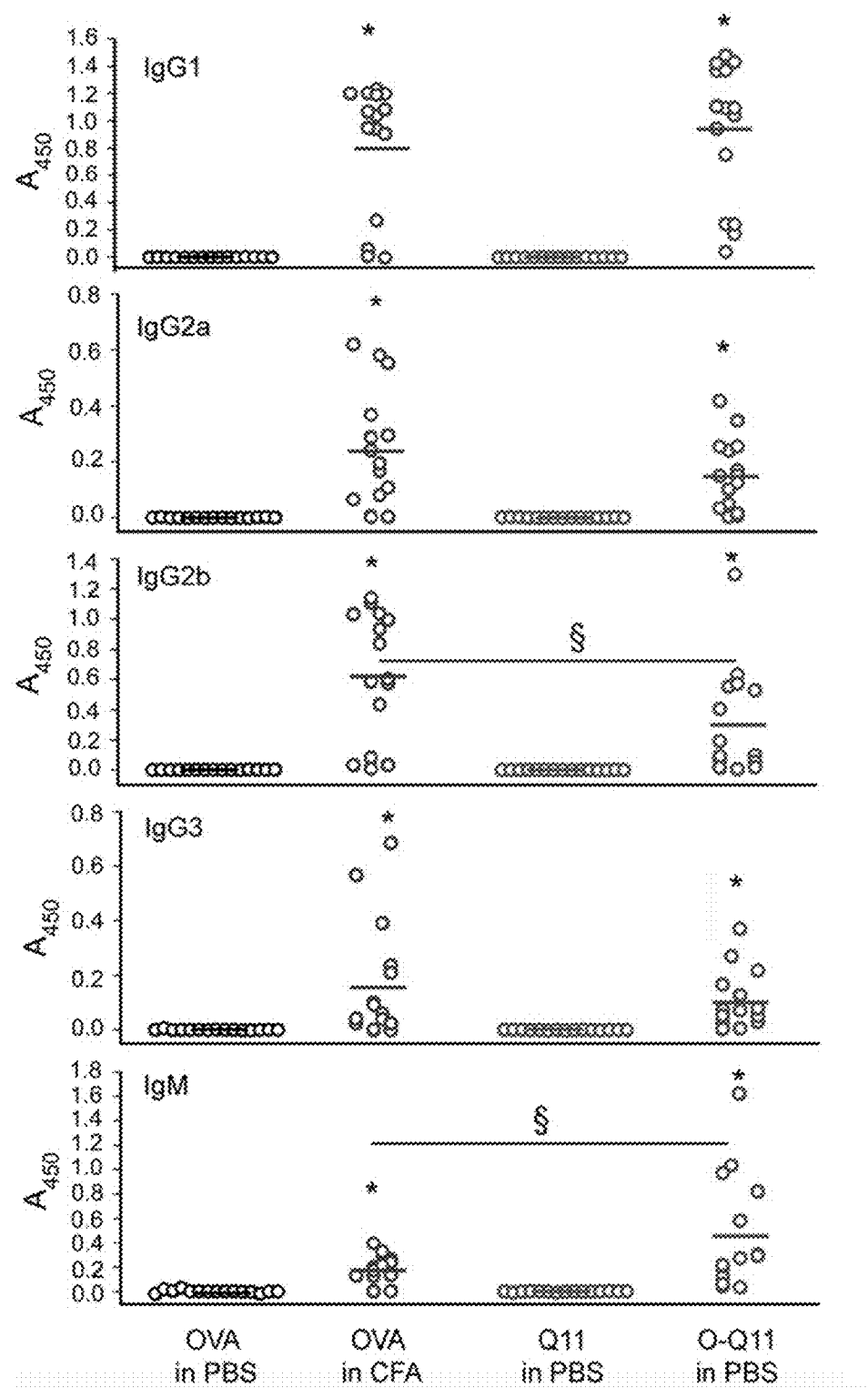
FIG. 4 Antibody isotypes in sera from mice immunized with peptides. Each point represents one mouse; bars represent the mean. *$p<0.01$ compared with OVA delivered in PBS by ANOVA with Tukey HSD post-hoc test. §$p<0.05$ as indicated.

To determine the nature of the immune response to Q11-adjuvanted peptides, the isotypes of the responding antibodies were evaluated. For both OVA in CFA and fibrillized 0-Q11, the dominant antibody isotype was IgG1, with smaller amounts of IgG2a, IgG2b, IgG3, and IgM being produced for both (FIG. 4). Comparing CFA-adjuvanted responses with Q11-adjuvanted responses, IgG1, IgG2a, and IgG3 were produced in statistically similar quantities, but IgG2b production was greater in the CFA-adjuvanted group, and IgM production was greater in the Q11-adjuvanted group.

Figures 5A, 5B, 5C:
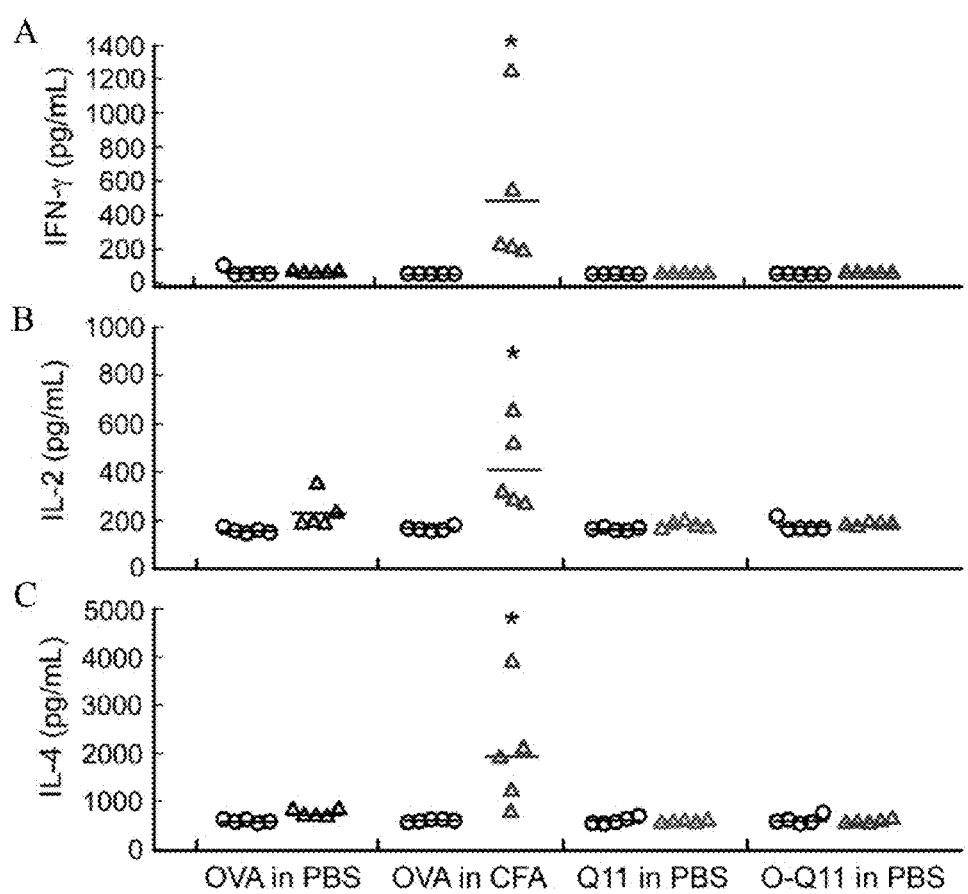
FIGS. 5A-5C IFN-γ, IL-2, and IL-4 production in peptide-challenged (triangles) and unchallenged (circles) splenocyte cultures. Each point represents one mouse; bars represent the mean. *$p<0.01$ compared with corresponding unchallenged control, by ANOVA with Tukey HSD post-hoc test.
Figure 6:
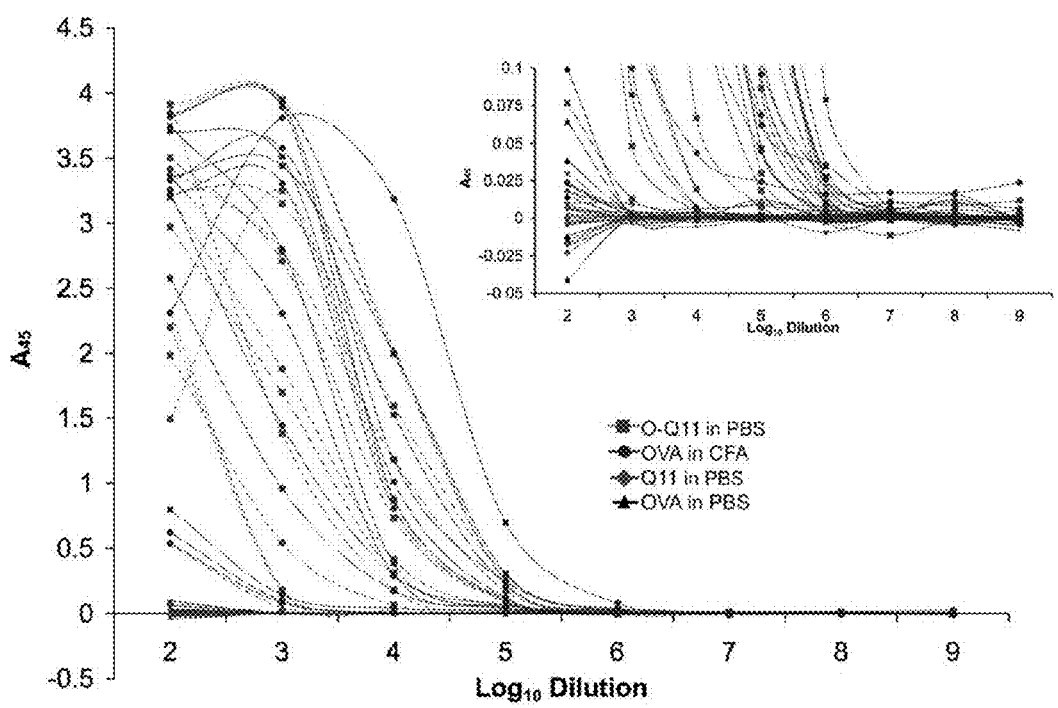
FIG. 6 Shows total IgG ELISA absorbance values for serially diluted serum from individual mice, corresponding to the titer calculations shown in FIG. 5. Each line represents one mouse. Mice receiving O-Q11 in PBS, OVA in CFA, Q11, and OVA in PBS are shown. The inset shows an expanded scale, for visualizing the low absorbance values of the Q11 and negative control mice.
Figure 7:
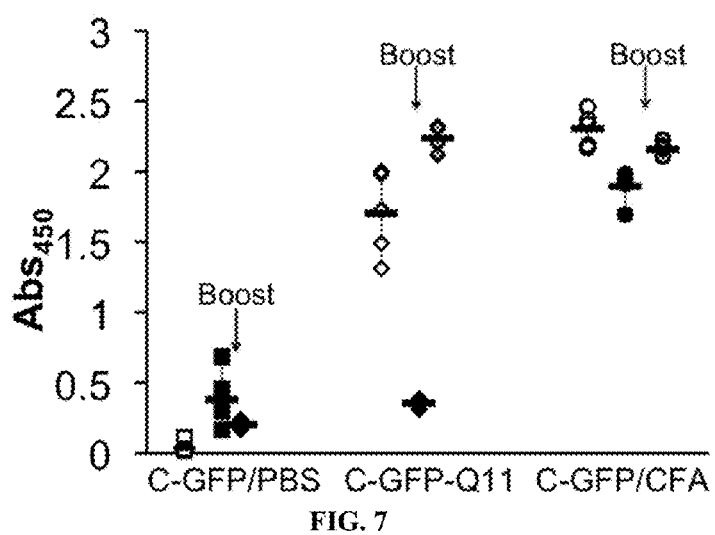
FIG. 7 Total IgG antibodies by mice immunized with GFP-cutinase-phosphonate-Q11 fibrils, cutinase-GFP emulsified in CFA, or cutinase-GFP in PBS.

To investigate the involvement of T cell help in the immune responses to O-Q11, splenocytes from immunized mice were challenged in vitro with the peptides, and the production of interferon-γ (IFN-γ), interleukin-2 (IL-2), and interleukin-4 (IL-4) was measured. These three cytokines were selected to provide measures of either a Th1 response (IFN-γ and IL-2) or a Th2 response (IL-4). However, somewhat surprisingly, when splenocytes from immunized mice were challenged in vitro with the immunizing peptide, they did not produce significant levels of any of these three cytokines compared with positive controls (FIG. 5).

Attaching a short self-assembling amino acid sequence to a peptide epitope's C-terminus can dramatically enhance the peptide's immunogenicity. The results indicate that fibrillizing peptide domains may be useful as simple adjuvant systems for peptide-based immunotherapies, and these results also provide guidance for the development of non-immunogenic peptide biomaterials within applications such as regenerative medicine. As a means to specifically enhance peptide immunogenicity, the novel Q11-based approach reported here has a number of non-limiting advantages. For example, a self-assembling peptide domain can be easily added to any known epitope using conventional solid phase peptide synthesis. Also, by utilizing self-assembly, highly multivalent nanoscale objects can be directly produced from only one molecule, which enables precision in the production, purity, and study of the material. In contrast, many adjuvants currently employed or under development are comprised of multiple molecular constituents or heterogeneous mixtures, making their definition, formulation, purification, and characterization challenging. For example, immunotherapies based on attenuated live viruses or heat-killed organisms contain intrinsic adjuvants such as lipopolysaccharide or unmethylated CpG motifs that are critical to their efficacy (McKee et al., 2007). Adjuvants based on natural products such as saponins or squalene (Sun et al., 2009) are by nature associated with some degree of molecular heterogeneity, and particulate adjuvants such as aluminum salts depend on antigen adsorption or entrapment, processes which are complexly dependent on multiple chemical and physical factors during formulation (Marrack et al., 2009; McKee et al., 2007). Accordingly, specific molecular features of current adjuvants are not easily adjusted independently within a given vaccine formulation, making it difficult both to optimize an immunotherapy as well as understand its mechanism of action. Such efforts will be greatly enhanced with the availability of chemically defined adjuvants.

B. Materials and Methods

Peptide Synthesis and Purification. Peptides were synthesized using standard Fmoc chemistry as previously reported (Jung et al., 2009; Jung et al., 2008). For TEM studies, O-Q11 was N-terminally biotinylated on-resin using biotin o-nitrophenyl ester. Peptides were purified using a Varian ProStar HPLC system, Grace-Vydac C18 reverse phase columns, and water-acetonitrile gradients. Peptide identity and purity were confirmed by MALDI-MS and HPLC, respectively (Table 3). Endotoxin levels of all immunizations were <0.3 EU/mL by LAL chromogenic endpoint assay (Lonza), well within acceptable limits (Table 3).

Circular Dichroism. An AVIV 202 CD spectrometer (Aviv Biomedical, NJ), 0.1 cm path length quartz cells, and initial disaggregation in TFA were employed as previously reported (Jung et al., 2009). Working concentrations were prepared in degassed water using Phe absorbance at 257 nm. Owing to peptide fibrillization and the resultant low CD signal strength, spectra below 220 nm could not be measured accurately and so are not reported.

Transmission Electron Microscopy. Peptides were dissolved in deionized water and mixed 6:1 with PBS to produce working peptide concentrations of 330 μM. After fibrillizing for 4h, peptides were applied to 400 mesh gold grids with carbon support films, negative-stained with 1% uranyl acetate, and imaged on a Tecnai F30 TEM. For gold staining, prior to negative-staining grids were placed upside-down on a droplet of blocking solution (0.2% acetylated BSA, 0.1% gelatin from cold water fish skin in PBS) for 5 min, then for 2 h on a droplet of 5 nm colloidal gold conjugated to streptavidin (Sigma). Grids were washed once with blocking solution, twice with PBS, and stained with 1% uranyl acetate.

Immunizations. Peptides were dissolved in sterile water (8 mM) and allowed to fibrillize overnight at 4° C. Stock solutions were then diluted in sterile, endotoxin-free PBS to working concentrations. Female C57BL/6 mice (6-8 weeks old, Taconic Farms, IN) were each given two 50 µL subcutaneous injections near the shoulder blades, each injection containing 100 nmol of peptide. CFA-adjuvanted groups received the same volume and total peptide dose, prepared by emulsifying peptide/PBS solutions 1:1 in CFA. Mice were boosted at 28 days with two additional 25 µL injections, each containing 50 nmol of peptide. CFA groups were boosted in incomplete Freund's adjuvant (IFA). Mice receiving mixtures of Q11 and OVA received 100 nmol of each peptide in the first injection and 50 nmol of each in the second. Seven days after the boost, the mice were sacrificed, and sera and spleens were harvested. In all animal work, institutional guidelines for the care and use of laboratory animals were strictly followed under a protocol approved by the University of Chicago's Institutional Animal Care and Use Committee.

Determination of antibody titers. High-binding ELISA plates (eBioscience) were coated with either 20 µg/mL peptide in PBS or PBS alone (for uncoated background subtraction) overnight at 4° C. Wells were blocked with 1% BSA/0.5% Tween 20 in PBS, and serial dilutions of serum between $1:10^2$ and $1:10^9$ were applied, followed by peroxidase-conjugated goat anti-mouse IgG (H+L) (Jackson Immuno Research). Washing steps were performed with 0.5% Tween 20 in PBS, plates were developed using TMB substrate (eBioscience), and absorbance values were read at 450 nm. To determine titers for each antiserum, background absorbance values from uncoated wells were subtracted from coated wells, and net absorbances were compared to cutoff values. The cutoff consisted of the mean plus three times the standard deviation of the negative control group (mice receiving OVA without adjuvant) for each corresponding dilution. Any sample dilutions having absorbances above this cutoff value were considered positive readings. The titer was considered as the highest dilution for which it and all lower dilutions had positive readings. If no positive dilutions were present the titer was considered to be $10^2$. Negative control mice (OVA without adjuvant) did not raise detectable IgG, and no single mouse in the negative control groups had absorbance values greater than three standard deviations above the group's mean for a given dilution; therefore all negative control mice are reported as having titers of $10^2$, which is the baseline level of detection for this study. Antibody isotypes were analyzed similarly using a mouse monoclonal antibody kit containing goat anti-mouse IgG1, IgG2a, IgG2b, IgG3, and IgM (Sigma).

Splenocyte isolation and challenge. Spleens of the immunized mice were pressed through 70 µm cell strainers, and isolated splenocytes were washed in RPMI medium containing 10% FBS. Red blood cells were lysed using ACK buffer (150 mM $NH_4Cl$, 10 mM $KHCO_3$/0.1 mM EDTA) and washed twice. $1 \times 10^6$ cells/well (96 well plate) were plated in complete T cell medium (S-MEM supplemented with 3.75 mM dextrose, 0.9% L-glutamine, 0.6% essential amino acids, 1.26% non-essential amino acids, 0.9% sodium pyruvate, 9 mM sodium bicarbonate, 95 µM gentamycin, 140 µM penicillin-G, 60 µM streptomycin sulfate, 44 µM 2-mercaptoethanol, and 10% fetal bovine serum) containing 5 µg/ml challenging peptide or no peptide. After a 24 h, interferon-γ (IFN-γ), IL-2, and IL-4 concentrations were measured in the culture medium using a sandwich ELISA. Antibodies and reagents were purchased from eBioscience, and cytokine concentrations were calculated from standard curves.

Statistical Analysis. Statistical analysis was performed by ANOVA with Tukey's HSD post hoc comparisons. The data reported in FIG. 3A and FIG. 4 represent three separate experiments, each containing five mice per group. Positive and negative controls were not statistically different between the three trials, and so the data were pooled into the groups of 15 shown.

Example 2

Characterization of Immune Responses to Q11 Linked Peptides

A. Results

Antibody responses to self-assembled peptide antigens are long-lived. In a previous study it was shown that conjugating an antigenic peptide (OVA) to the self-assembling peptide domain Q11 results in robust antibody responses against OVA. It was found that mice immunized with 100 nmol of the fibrillized antigen elicited similar antibody titers as the free peptide administered in complete Freund's adjuvant (CFA). The dose dependence and longevity of the antibody response to OVA-Q11 was further investigated and antibody responses against the malarial peptide epitope $(NANP)_3$ coupled to Q11 were also characterized. Mice were immunized with two different doses of OVA-Q11 (100 nmol and 50 nmol), or 100 nmol of (NANP)$_3$-Q11 and boosted with half the dose at wk 4. Mice were bled on a weekly basis up to wk 6, once at wk 8, and once every four weeks thereafter.

Serum ELISAs indicated that antibody production was long-lived, as antibodies were detectable for at least 36 wks in OVA-Q11-immunized mice. Similar levels were detected in OVA peptide delivered in CFA. The antibody levels spiked approximately 2.5 fold after the boost at wk 4 and reached maximum levels around wk 6 in the OVA-Q11 immunized mice for both the 100 nmol and 50 nmol groups. Although the antibody production at earlier time points (wk 3 and wk 4) was higher in the 100 nmol group, no significant difference was observed after the boost and throughout the duration of the study. This suggested that immunizing mice with 50 nmol of OVA-Q11 elicited antibody responses with similar magnitude and longevity as mice immunized with 100 nmol of OVA-Q11.

Mice immunized with $(NANP)_3$-Q11 also elicited sustained antibody responses that were detectable for up to 28 wks; however, unlike OVA-Q11 no spike in antibody levels was observed after the boost. These results demonstrate that self-assembled peptides decorated with peptide antigens can elicit long term antibody production in mice without the need for frequent boosting.

Co-assembled peptide antigens elicit immune responses independently. Transmission electron microscopy showed that OVA-Q11, $(NANP)_3$-Q11, and co-assembled OVA-Q11/$(NANP)_3$-Q11 self-assembled into fibers in phosphate buffered saline. To investigate if antibodies were raised simultaneously against multiple self-assembled antigens co-administered in vivo, mice were immunized with OVA-Q11 and $(NANP)_3$-Q11 either separately or as co-assembled fibrils. The total peptide concentration was the same in both groups. Injecting the peptides either separately or as co-assembled fibrils, resulted in production of antibodies against both epitopes. Antibodies were produced for up to 16 wks with similar magnitudes, suggesting that the presence of one peptide did not alter immune responses towards the other. Interestingly, the spike in the antibody levels of OVA-Q11 at wk 5 was not observed. However, there was a small increase in the antibody levels in NANP-Q11 boosted mice at wk 5 in both groups, which was not detected when mice were immunized with (NANP)$_3$-Q11 alone.

Antibodies generated against self-assembled peptides cross-reacted with whole proteins. For efficient protection against disease antibodies raised against single epitopes must react with and neutralize whole proteins or pathogens. To determine if the antibodies produced against self-assembled OVA peptide reacted with whole ovalbumin, serum derived from OVA-Q11 immunized mice was applied to ELISA plates coated with OVA-Q11 or ovalbumin. Antibodies raised against OVA-Q11 were reactive against ovalbumin.

Peptide Assemblies were observed in the lymph nodes for extended time periods. Immunohistochemistry data and staining for biotin on the peptides indicated that OVA-Q11 was localized to the draining lymph nodes over time. Peptide assemblies (stained brown and indicated by arrows) were found at the cortex of the lymph nodes by wk 1 and continued to persist up to wk 6. No peptide was observed at time points earlier than one week (1 day and 3 days). Although the mechanism of trafficking is unknown, co-staining for macrophages, dendritic cells, or B cells might provide further insights into the uptake and processing of these peptides in vivo.

Antibody responses to self-assembled peptides are T cell-dependent. The robust antibody responses and isotype class switching observed with OVA-Q11 suggested involvement of CD4+ T cells. To determine the requirement for T cells, an adoptive T cell transfer assay was performed. Specifically, mice were injected with CFSE labeled DTII cells, which express receptors for the H-$2^b$ restricted OVA epitope. Antigen-mediated proliferation causes a decrease in the CFSE intensity which can be detected by flow cytometry.

Robust proliferation of DTII cells in the OVA-Q11 and OVA-CFA immunized mice was observed by the shift in the CFSE intensity peak which demonstrated that T cells were involved in the immune responses against OVA-Q11. Quantifying the shift in the CFSE intensity indicated that more than 95% of the transferred cells in both OVA-Q11 and OVA-CFA immunized mice proliferated. In contrast, a negligible shift in CFSE intensity was observed for Q11-immunized mice. The extent of proliferation was found to be similar in both the spleen and the lymph nodes. Immunization with OVA-Q11 after adoptive transfer of OTII cells elicited rapid antibody production compared to mice that were not given OTII cells. Interestingly, mice that were injected with OTII cells and immunized OVA-CFA failed to generate antibody responses within the same time frame.

To confirm the necessity of T cells, KO mice lacking both the αβ and γδ receptors for CD4$^+$ T cells were immunized with OVA-Q11 along with wild type controls. No antibody production was observed in mice lacking the T cell receptors over 6 wks suggesting that T cells are required for antibody production against OVA-Q11. The wild type control mice responded as expected. Together, these data support the earlier T cell requirement conclusion. To ensure that the KO mice are capable of eliciting immune responses, they were immunized with a T-independent antigen, NP-Ficoll. Antibody production against NP-Ficoll was observed in the KO mice demonstrating their capability to mount B cell-mediated immune responses and reconfirming that antibody responses against OVA-Q11 were T cell-mediated. This finding might not be surprising because OVA is a strong MHC class II peptide, containing both B and T cell determinants. To further determine if T cells are required for other epitopes, T cell receptor KO mice were immunized with (NANP)$_3$-Q11 which resulted in no antibody production. These findings suggest that CD4$^+$ T cells might play an important role in the immune responses against self-assembled antigens.

B. Materials and Methods

Peptide Synthesis and Purification Peptides were synthesized on a CSBio136-XT peptide synthesizer using standard Fmoc chemistry, cleaved using cocktail solution (95% trifluoroacetic acid, 2.5% water and 2.5% triisopropyl silane), precipitated in diethyl ether, and lyophilized. Peptides were purified using a Varian ProStar HPLC system, Grace-Vydac C18 reverse phase columns, and water/acetonitrile gradients. The acetonitrile was removed by centrifugal evaporation and the peptides were lyophilized and stored at −20° C. until further use. Peptide identity and purity were confirmed by MALDI-MS and HPLC, respectively. Endotoxin levels of all formulations were tested using a Limulus Amebocyte Lystae (LAL) chromogenic end point assay (Lonza, USA). Endotoxin levels in all immunization formulations were found to be less than <0.22 EU/mL. The peptides synthesized were NANPNANPNANPSGSGQQKFQFQFEQQ ((NANP)$_3$-Q11 (SEQ ID NO:27)), and ISQAVHAAHAEINEAGRSGSGQQKFQFQFEQQ (OVA-Q11 (SEQ ID NO:28)).

Transmission Electron Microscopy Stock solutions of 1 mM peptides were allowed to fibrillize in PBS for 4 h at room temperature or overnight at 4° C., diluted to 0.25 mM, and pipetted onto carbon-coated 200 mesh lacey grids (Electron Microscopy Sciences). For the co-assembled fibrils, OVA-Q11 and (NANP)$_3$-Q11 peptides were mixed as dry powders, dissolved in deionized water, and diluted in PBS to produce working peptide concentration of 0.5 mM. After fibrillizing for 4 h, peptides were applied to the grids. The grids were stained with 1% uranyl acetate for 2 minutes, and imaged with a FEI Tecnai F30 transmission electron microscope.

Animals and Immunizations Peptides were dissolved in sterile water (8 mM stock), incubated overnight at 4° C., and diluted in sterile PBS (2 mM working concentration) prior to immunizations. For the malaria peptide, (NANP)$_3$-Q11, the formulations were incubated in PBS overnight to ensure complete fibril formation. To prepare co-assembled fibers of OVA-Q11/(NANP)$_3$-Q11 or OVA-Q11/Biotin-Q11, the peptides were combined as dry powders, mixed thoroughly, and dissolved in sterile water. The peptides were allowed to co-assemble overnight at 4° C. and fibrillized in sterile PBS. Female C57BL/6 mice (6-8 weeks old, Taconic Farms, IN) were immunized subcutaneously with two 50 μL injections in the back, with each injection containing 100 nmol of peptide. Mice were boosted at 28 days with two additional 25 μL injections, each containing 50 nmol of peptide. Blood was drawn on a weekly basis via the submandibular maxillary vein, the serum extracted, and stored at −80° C. until use. To identify local tissue responses and peptide distribution, mice were injected intramuscularly with 50 μL of peptide solution (90% OVA-Q11+10% Biotin-Q11) in each thigh and the muscles and inguinal lymph nodes were extracted at predetermined time points. In all animal work, institutional guidelines for the care and use of laboratory animals were strictly followed under a protocol approved by the University of Chicago's Institutional Animal Care and Use Committee.

Determination of Antibody Production ELISA plates (eBioscience) were coated with 20 µg/mL of peptide or 0.5 µg/mL of whole protein in PBS overnight at 4° C. The plates were blocked with 200 µL of 1% BSA in PBST (0.5% Tween-20 in PBS) for 1 h and serial dilutions of serum between $1:10^2$ and $1:10^9$ were applied (100 µL/well) for 1 h at room temperature. Peroxidase-conjugated goat anti-mouse IgG (H+L) (Jackson Immuno Research) (1:5000 in 1% BSA-PBST, 100 µL/well) was then applied for 30 min and the plates were developed using TMB substrate (100 µL/well, eBioscience). The reaction was stopped using 50 µL of 1 M phosphoric acid and 100 µL of the solution was transferred to fresh plates and absorbance values were read at 450 nm. Absorbance values of PBS (no antigen) coated wells were subtracted to account for background. The plates were washed between each step with PBST.

Immunohistochemistry Freshly dissected skeletal muscle and inguinal lymph nodes were fixed overnight with 4% formaldehyde in phosphate-buffered saline (pH 7.2) and the tissue was processed and embedded in paraffin at the Human Tissue Resource Center (University of Chicago). The paraffin blocks were cut on a microtome (Leica, USA) into 4 µm thick sections and were deparaffinized with xylene and rehydrated with gradient ethanol. The sections were boiled in 10 mM sodium citrate solution (pH 6.0) for 10 min to retrieve the antigens and blocked with 5% BSA in PBS for 1 hr. The sections were then incubated with Horseradish Peroxidase Avidin D (Vector Laboratories, CA) for 3 hrs, and the biotin was visualized using a peroxidase substrate diaminobenzidine kit (Vector Laboratories, CA). The sections were also counterstained with Mayer's hematoxylin solution (Sigma-Aldrich, USA) for 10 mins. The slides were dehydrated with gradient ethanol and xylene and mounted with Permount Mounting Medium (Fisher Scientific, PA). Images were acquired using a Zeiss Axioskop at the Microscopy Core Facility (University of Chicago).

Adoptive Transfer of T cells OTII transgenic mice on C57BL/6 background, whose T cells recognize the OVA peptide and carry a marker to distinguish them from naïve T cells from B6 mice (CD90.1 congenic). In vivo CD4+ T cell proliferation was analyzed after adoptive transfer into mice and immunization with the peptides. Briefly, splenocytes and lymph nodes of OTII+ C57BL/6 mice were processed into a single cell suspension and enriched for CD4+ T cells, by negative magnetic separation (Miltenyi Biotec). The cells were then labeled with 10 µM carboxyfluorescein succinimidyl ester (CFSE) and adoptively transferred into mice ($5 \times 10^5$ OTII cells/mouse, retroorbital injection) 24 h before peptide immunizations. The next day, mice were immunized with 100 nmol of OVA-Q11 in PBS, OVA in CFA, or Q11 in PBS at two different sites subcutaneously. Five days after immunizations, spleens and lymph nodes were harvested, processed into single cell suspensions, and stained for flow cytometry in 1% BSA in PBS containing 0.02% sodium azide (FACS buffer) for 1 hour at 4° C. with APC-labeled anti-CD4 (RM 4-5) (BD Biosciences, NJ) and PECy7-labeled anti-CD90.1 (HIS51) (eBioscience, CA) respectively. Anti-CD16/32 (2.4G2.1) (University of Chicago Immunology Core) was used to prevent nonspecific antibody binding. After staining, cells were washed twice with FACS buffer and samples were run on the LSR-II (BD Biosciences, NJ) flow cytometer and analyzed for evidence of proliferation as indicated by dilution of CFSE intensity using. FlowJo cytometry analysis software (Tree Star, OR) was used to analyze and quantify the results. Blood was collected through cardiac exsanguinations and serum was extracted and stored at −80° C. until further use.

Example 3

Modification of Fibril Monomers

A. Results.

Synthesis of Phosphonate-Q11. MALDI-TOF-MS analysis demonstrated that phosphonate-Q11 can be synthesized in good yield by reacting phosphonate-maleimide with cys-terminated Q11. Similar to Q11, phosphonate-Q11 self-assembled into fibrils when dissolved in 1× PBS at a concentration of 0.25 mM.

Cutinase-GFP Reacts Efficiently with Mixed Q11: Phosphonate-Q11 Fibrils. The reaction of cutinase with phosphonate results in the release of p-nitrophenol, which absorbs light at 403 nm. The absorbance of solutions containing 1 mM Q11:phosphonate-Q11 (99:1 molar ratio) and 4.5, 9, or 15 µM cutinase-GFP at 403 nm increased as a function of time. Absorbance values reached a plateau for the 4.5 µM cutinase-GFP condition by 300 minutes, which suggested that the reaction approached completion over this time frame. For the 9 and 15 µM cutinase-GFP conditions, a time course of nearly 600 minutes was required for these reactions to approach completion.

To characterize the extent of reaction between cutinase-GFP and phosphonate-Q11, unreacted cutinase-GFP was removed from the peptide fibrils by serial centrifugation washes and then measured the fluorescence intensity of the purified fibrils. When 0.9 µM or 1.8 µM cutinase-GFP was reacted with 1 mM Q11:phosphonate-Q11 (99:1 molar ratio), the fluorescence intensity of fibrils was similar to the fluorescence of cutinase-GFP in 1× PBS at the same concentration, suggesting that the reaction proceeds nearly quantitatively under these conditions. When the cutinase-GFP concentration was increased to 4.5, 9 or 15 µM, however, the resulting fibril fluorescence intensity was equal to GPF concentrations of 2.5, 4.12 or 4.75 µM, respectively, which corresponds to an extent of reaction of approximately 50% for each condition. This suggests that as stoichiometric ratios of cutinase and phosphonate are reached, the extent of reaction is limited by phosphonate moiety availability, which may be influenced by packing of protein onto the fibrils (i.e. a steric limit) or burying of phosphonate moieties within the fibrils during assembly.

The influence of fibril preparation on the reaction between phosphonate-Q11 and cutinase-GFP was also characterized. The reaction kinetics and extent of reaction between cutinase-GFP and phosphonate-Q11 were similar for two different cutinase-GFP concentrations, regardless of whether the fibrils were prepared by mixing an aqueous solution of Q11 with an aqueous solution of phosphonate-Q11 at a 99:1 volume ratio or by dissolving a mixture consisting of a 99:1 molar ratio of dry Q11 and phosphonate-Q11, illustrating robustness in formulating the materials.

Mice immunized with GFP-Q11 fibrils produced antibodies against cutinase-GFP. CB57BL/6 mice immunized with 3.58 µM GFP-cutinase conjugated to 1 mM Q11:phosphonate-Q11 fibrils (99:1 molar ratio) produced IgG antibodies that were reactive against microtiter plates coated with GFP-cutinase-phosphonate-Q11 fibrils by 1 week post-immunization. The amount of total IgG produced by these mice increased by week 2, and then decreased at week 3 and 4. Compared to mice injected with GFP-cutinase emulsified in complete Freund's adjuvant, a commonly used potent adjuvant in mouse models, the total amount of IgG antibodies produced by mice immunized with GFP-cutinase conjugated to mixed Q11:phosphonate-Q11 fibrils were lower, however, the trajectory of antibody production was similar in both groups. Importantly, mice immunized with GFP-cutinase in 1× PBS demonstrated low levels of antibody production through 4 weeks, indicating that the observed antibody production in mice immunized with GFP-cutinase conjugated to mixed Q11:phosphonate-Q11 fibrils is not due to the injection of foreign proteins into the mice, but rather requires the action of an adjuvant.

Mice were boosted with a half dose of GFP-cutinase conjugated to Q11:phosphonate-Q11 fibrils (99:1 molar ratio) at day 31, which resulted in increased IgG antibody levels that were maintained through week 6. The total IgG produced post-boost was similar in mice immunized and boosted with GFP-cutinase conjugated to mixed Q11:phosphonate-Q11 fibrils or mice immunized with GFP emulsified in CFA and boosted with GFP-cutinase emulsified in incomplete Freund's adjuvant. This suggested that chemically-defined self-assembled fibrils decorated with protein antigens are as effective as ill-defined oil emulsions as adjuvants for prime-boost vaccination strategies.

To determine the reactivity of antibodies produced by mice immunized with GFP-cutinase conjugated to mixed Q11:phosphonate-Q11 fibrils serum collected at week 5 was reacted with ELISA plates coated with GFP-cutinase-phosphonate-Q11 fibrils or GFP-cutinase. Antibody reactivity against toward both plates was similar, which indicates that the antibodies produced around week 5 are primarily reactive towards the GFP-cutinase fusion protein and are relatively unreactive towards the mixed Q11:phosphonate-Q11 adjuvant.

Antibody isotype is an important indicator of the immunological pathways involved in antibody production. IgG1 was the prominent isotype in serum collected at week 5 from mice immunized with GFP-cutinase conjugated to mixed Q11:phosphonate-Q11 fibrils, while lower levels of IgG2a, IgG2b, IgG3, or IgM were also present. Interestingly, while IgG1 was also the major antibody isotype present in serum collected from mice immunized with GFP-cutinase emulsified in CFA at week 5, IgG2b was also elevated compared to other isotypes. The predominance of IgG1 suggests that for both adjuvants, antibody production involves Th-2 mediated, IL-4-dependent, B cell isotype switching.

B. Materials and Methods

Cutinase-GFP expression. Origami B (DE3) *E. coli* transformed with the cutinase-GFP fusion vector were cultured in 10 mL 2XTY media with 100 µg/mL carbenicillin and 50 µg/mL kanamycin A overnight at 37° C. on a rotary shaker at 2200 rpm. After overnight culture, *E. coli* were subcultured into a 1 L flask containing 2XTY media with 100 µg/mL carbinocillin and 50 µg/mL kanamycin A. The flask was incubated at 37° C. in a rotary shaker at 2200 rpm and the cells were allowed to proliferate until reaching an optical density at 600 nm of 0.6-0.8. When the *E. coli* reached an appropriate density, expression of cutinase-GFP was induced by adding 0.5 mM isopropyl β-D-1-thiogalactopyranoside (IPTG) to the medium. IPTG-induced cells were cultured for 16 hours at 18° C. on a rotary shaker at 2200 rpm. At the end of the expression period, cells were pelleted by centrifugation at 9800 rpm for 10 minutes. Media was decanted from the pellet and *E. coli* was washed once by resuspending in 400 mL of buffer containing 50 mM Tris-HCl, 3 mM $MgCl_2$, 250 mM NaCl (Buffer A) followed by centrifugation at 9800 rpm for 10 minutes. Following centrifugation, buffer A was decanted from the pellet, *E. coli* was resuspended in 35 mL buffer A, and *E. coli* was transferred to a 50 mL conical tube. *E. coli* were lysed to release cutinase-GFP by adding 3.5 mL 10× BugBuster, 300 units DNAse, and one eComplete mini EDTA-free protease tablet to the buffer and incubating for 20 minutes at room temperature on a table-top shaker. Cell debris was separated from GFP-cutinase by centrifuging the lysis buffer at 20000 rpm, 4° C. for 35 minutes. $His_6$-tagged cutinase-GFP was further purified by column chromatography by passing the centrifugation supernatant over a cobalt column. The column eluent was collected and passed over the column a second time to increase yield of GFP-cutinase recovered. Protein bound to the cobalt column was washed with 10 column volumes of buffer A. Protein was eluted from the column by passing 50 column volumes of Buffer A containing 0.5% Triton X-100 over the protein-bound column. The eluted protein was dialyzed overnight at 4° C. against buffer containing 25 mM Tris-HCl, 150 mM NaCl, 0.05% $NaN_3$, pH 7.8 to exchange salts and remove endotoxin bound to Triton X-100. Protein was concentrated by centrifugation using an Amicon Ultra centrifugal filter. Protein molecular weight was analyzed by SDS-PAGE. GFP activity was characterized by exposing the protein to a 395 nm UV light and cutinase activity was characterized by incubating protein in 1× phosphate-buffered saline (pH 7.4) containing dinitrophenol and measuring absorbance at 405 nm. Protein was stored in buffer at 4° C. or −20° C. until use.

Endotoxin quantification and removal. Endotoxin level in GFP-cutinase was quantified using a Limulus amebocyte lysate assay according to manufacturer's instructions. Endotoxin was removed from GFP-cutinase by: (1) adding cold Triton X-114 at a 1:10 (v/v) ratio to a solution of GFP-cutinase, (2) incubating this solution on ice for 10 minutes, (3) incubating this solution at 37° C. for 20 minutes to precipitate endotoxin-loaded Triton X-114 micelles, (4) centrifuging at 4000 rpm for 5 minutes, and (5) collecting the endotoxin-free supernatant containing GFP-cutinase. This process was repeated once to ensure removal of endotoxin.

Phosphonate-Q11 synthesis—The peptides Q11 or C-SGSG-Q11 were synthesized on a CSBio 136-XT using a standard solid phase peptide synthesis protocol based on Fmoc-protected α-amine and HOBt, HBTU, DIEA activation. Peptide was cleaved from the resin by incubating in a cocktail containing 95% trifluoroacetic acid, 2.5% triisopropylsilane, and 2.5% water for 90 minutes. At the end of the cleavage reaction, the cocktail was passed through a filter to separate the peptide from the synthesis resin. The cocktail was then removed using a rotary evaporator and cold diethyl ether was added to precipitate the peptide. The peptide precipitate was collected by centrifuging at 3500 rpm for 5 minutes, the supernatant was decanted off, and the peptide was washed with cold ether. This process was repeated 5×. After the final centrifugation step, the peptide was dried over vacuum for 60 minutes, dissolved in 25 mL deionized water, frozen, and lyophilized to dryness. The dry peptide was analyzed by MALDI-TOF-MS. Peptide was purified to greater than 95% purity using an acetonitrile/water gradient on a Varian ProStar HPLC system equipped with a Grace-Vydac C18 reverse phase column. For phosphonate-Q11 synthesis, C-SGSG-Q11 was first dissolved in DI $H_2O$. DMSO containing maleimido-EG6-ethyl-p-nitrophenyl phosphonate was then added to the aqueous C-SGSG-Q11 solution and the reaction was allowed to proceed at 37° C. for 2 hours. At the end of the reaction, the solution was loaded directly onto a reverse-phase semi-prep scale C18 column and purified with a linear gradient of 75% can in DI $H_2O$+0.1% Trifluoroacetic acid over 1 hour. Fractions were lyophilized to dryness and analyzed with MALDI-TOF-MS.

Transmission Electron Microscopy—A 1 mM peptide solution was allowed to fibrillize in PBS for 4 h at room temperature or overnight at 4° C., at which point it was diluted to 0.25 mM and pipetted onto carbon-coated 200 mesh lacey grids (Electron Microscopy Sciences). The grids were stained with 1% uranyl acetate for 2 minutes, and imaged with a FEI Tecnai F30 transmission electron microscope.

Reacting phosphonate-Q11 fibrils with cutinase-GFP—Dry Q11 and phosphonate-Q11 were dissolved in deionized water at a 99:1 molar ratio to achieve a final concentration of 10 mM. 1×phosphate-buffered saline was added to the aqueous peptide solution to achieve a final concentration of 1.1 mM. A buffered solution containing 150, 90, 45, 18, or 9 μm GFP-cutinase was added to the buffered peptide solution to achieve a final peptide concentration of 1 mM and a final protein concentration of 15, 9, 4.5, 1.8, or 0.9 μM. The reaction between cutinase-GFP and phosphonate-Q11 was allowed to proceed at room temperature for at least 10 hours. The extent of reaction between phosphonate-Q 11 and cutinase-GFP was monitored by measuring the absorbance of the solution at 403 nm at specified time intervals. At the reaction end-point, unreacted cutinase-GFP was removed from the cutinase-GFP-modified fibrils by centrifuging the reaction solution at 13000 rpm for 5 min, removing 70% of the supernatant with a pipet, replacing the removed volume of supernatant with fresh 1×PBS, and resuspending the fibril pellet by pipetting. This process was repeated 5 times to ensure removal of unreacted protein. After removing unreacted cutinase-GFP, the concentration of cutinase-GFP conjugated to phosphonate-Q11 fibrils was quantified by measuring fluorescence intensity using a 395/509 (excitation/emission) filter set and comparing the fluorescence intensity readings to those collected from a standard curve of GFP fluorescence.

Immunization protocols—1 mM Q11:phosphonate-Q11 (99:1 molar ratio) and 4.5 μm cutinase-GFP were mixed under sterile conditions and allowed to react overnight at room temperature. Unreacted cutinase-GFP was removed from the fibrils and the concentration of cutinase-GFP conjugated to fibrils was determined using the methods outlined above. For this particular study, the concentration of cutinase-GFP conjugated to fibrils was determined to be 3.58 μm. At day 0, C57BL/6 mice (n=5) were immunized by subcutaneously injecting 50 μL of the cutinase-GFP conjugated fibril solution into each of two flanks (100 μL total injection volume). At this same time point, separate groups of C57BL/6 mice (n=5) were also immunized by subcutaneously injecting 50 μL of solution containing 7.16 μm cutinase-GFP emulsified with complete Freund's adjuvant at a 50/50 (v/v) ratio (positive control) or 3.58 μm cutinase-GFP in 1× PBS (negative control) into each of two flanks (100 μL total injection volume). At day 31, mice were boosted by subcutaneously injecting 25 μL of the cutinase-GFP conjugated fibril solution, 7.16 μm cutinase-GFP emulsified with incomplete Freund's adjuvant at a 50/50 (v/v) ratio (positive control) or 3.58 μm cutinase-GFP in 1× PBS (negative control) into each of two flanks (50 μL total injection volume). Blood was drawn from each mouse weekly, serum was separated from the blood by centrifugation, and total serum IgG was quantified by ELISA. For ELISAs, microtiter plates were coated overnight at 4° C. with 100 μL of either cutinase-GFP-phosphonate-Q11 fibrils or cutinase-GFP. Control wells were incubated with 100 μL of 1×PBS. After overnight coating, plates were washed 3× with 1× PBS containing 0.05% (v/v) Tween-20 (PBST). Plates were blocked with 0.1% bovine serum albumin in PBST (BSA-PBST) for 2 hours at room temperature. Serum was serially diluted 1:100 to 1:100000000 in BSA-PBST and 100 μL of each serum dilution was added to antigen-coated wells or control wells immediately after BSA blocking Serum antibodies were allowed to bind to the plates for 60 minutes at room temperature, at which point plates were washed 5× with PBST. 100 μL of horseradish peroxidase-conjugated goat anti-mouse IgG (1:5000 dilution) in BSA-PBST was added to the wells. After a 45 minute incubation at room temperature, wells were washed 5× with PBST. 100 μL 1×TMB substrate was then added to the wells and allowed to react for 5 minutes at room temperature. At the reaction-endpoint, the reaction was quenched by adding 50 μL 1 M $H_3PO_4$ to the wells. 100 μL of each solution was then transferred to a new well of a microtiter plate and the absorbance of each solution at 450 nm was measured using a plate reader. Absorbance from control wells was subtracted from absorbance from antigen coated wells and these resulting values, as well as their associated mean, were plotted for each time point.

Example 4

Peptide Nano Fibers Composed of D-Amino Acids Elicit Inverse Antibody and CD8 T Cell Responses Compared to their Enantiomeric Counterparts Peptide Synthesis and Purification. All peptides (sequences in Table S1) were synthesized using standard Fmoc Chemistry on a CS Bio-CS336X solid phase peptide synthesizer Rink Amide MBHA or Wang resin was swelled in dry DMF for 1hr, and peptides were double coupled using HBTU (O-(Benzotriazol-1-yl)-N,N,N',N'-tetramethyluronium hexafluorophosphate) and HOBt (1-Hydroxybenzotriazole) chemistries. Peptides were cleaved from the resin using 95% TFA/2.5% $H_2O$/2.5% triisopropyl silane cocktail and washed in diethyl ether. The crude product was purified by reverse-phase HPLC (C18 column) using Acetonitrile/$H_2O$ gradients to >90% purity and peptide mass was confirmed by MALDI using α-cyano-4-hydroxycinnamic acid matrix (Bruker Daltonics, MA). All peptides were lyophilized and stored at 4° C. Endotoxin levels of all peptides were tested using a limulus amebocyte lystae (LAL) chromogenic end point assay (Lonza, USA) at the same volume and peptide concentration used for immunizations and were found to be less than 0.11 EU/mL and within acceptable limits (Mlyala, et al., 2008). To account for batch-to-batch variability three different sets of peptides were synthesized for immunizing mice.

TABLE 4

List of peptides investigated in this study. The abbreviations, peptide sequences, theoretical mass, and observed mass are shown.

| Peptide | Sequences | SEQ ID NO: | Cal. $[M + H]^+$ | Obs. $[M + H]^+$ |
|---|---|---|---|---|
| KFE8 (L) | Ac-FKFEFKFE-Am | 25 | 1161.57 | 1162.02 |
| KFE8 (D) | Ac-$^DF^DK^DF^DE^DF^DK^DF^DE$-Am | 63 | 1161.57 | 1162.60 |
| OVA | H2N-ISQAVHAAHAEINEAGR-OH | 26 | 1773.90 | 1774.77 |

TABLE 4-continued

List of peptides investigated in this study. The abbreviations, peptide sequences, theoretical mass, and observed mass are shown.

| Peptide | Sequences | SEQ ID NO: | Cal. $[M + H]^+$ | Obs. $[M + H]^+$ |
|---|---|---|---|---|
| SIN | H2N-SIINFEKL-OH | 59 | 963.12 | 964.13 |
| SIN-KFE8 (L) | H$_2$N-FKFEFKFEGGAAYSIINFEKL-Am | 64 | 2483.27 | 2508.74 |
| SIN-KFE8 (D) | H$_2$N-$^D$F$^D$K$^D$F$^D$E$^D$F$^D$K$^D$F$^D$EGGAAYSIINFEKL-Am | 65 | 2483.27 | 2512.23 |
| OVA-KFE8 (L) | H$_2$N-ISQAVHAAHAEINEAGRSGSGFKFEFKFE-Am | 66 | 3164.46 | 3164.58 |
| OVA-KFE8 (D) | H$_2$N-ISQAVHAAHAEINEAGRSGSG$^D$F$^D$K$^D$F$^D$E$^D$F$^D$K$^D$F$^D$E-Am | 67 | 3164.46 | 3165.02 |

Figures 8A, 8B:
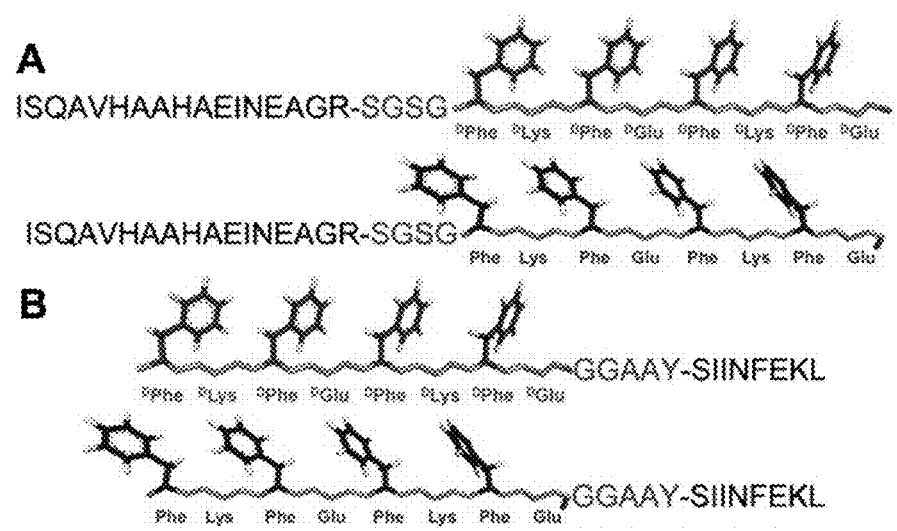
FIG. 8A-8B. Schematic of self-assembling peptide enantiomers KFE8(L) and KFE8(D) showing the position of the epitopes and linker sequences. (A) OVA epitope was linked to the N-terminus of the enantiomers using -SGSG- linker (SEQ ID NO: 67; SEQ ID NO: 66) and (B) SIN epitope was linked to the C-terminus through -GGAAY- (SEQ ID NO: 60) linker (SEQ ID NO: 65; SEQ ID NO: 64).
Figures 9A, 9B, 9C, 9D, 9E, 9F:
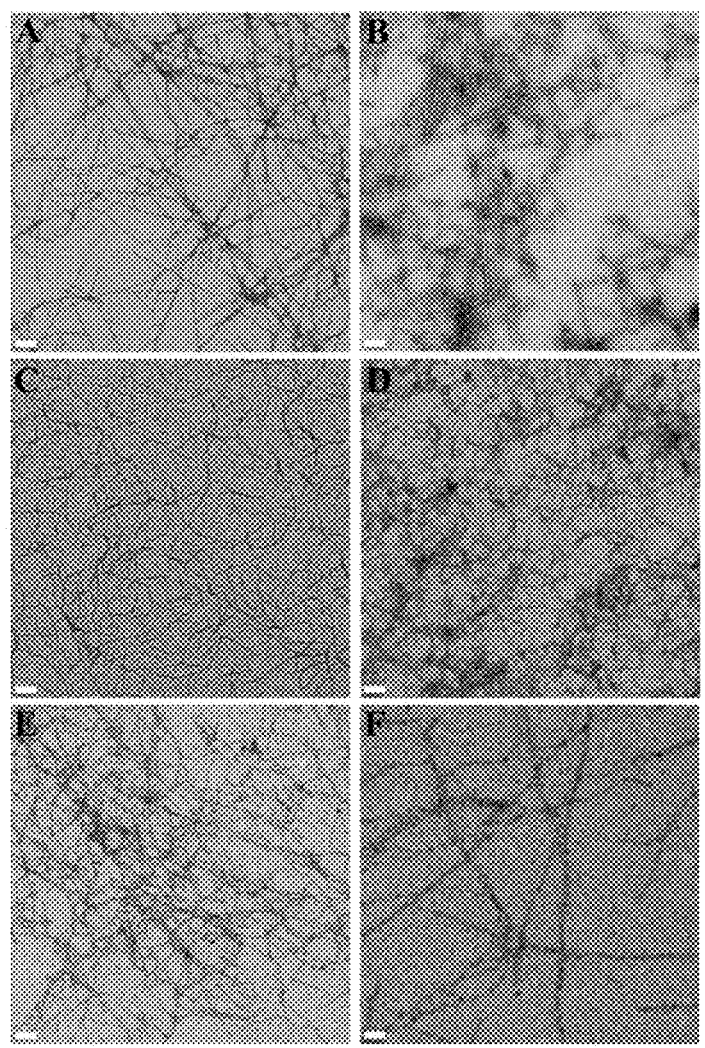
FIG. 9A-9F. Electron micrographs of self-assembling peptide enantiomers. TEM images of (A) KFE8(L), (B) KFE8(D), (C) OVA-KFE8(L), (D) OVA-KFE8(D), (E) SIN-KFE8(L) and (F) SIN-KFE8(D). Scale bar is 50 nm.
Figures 10A, 10B:
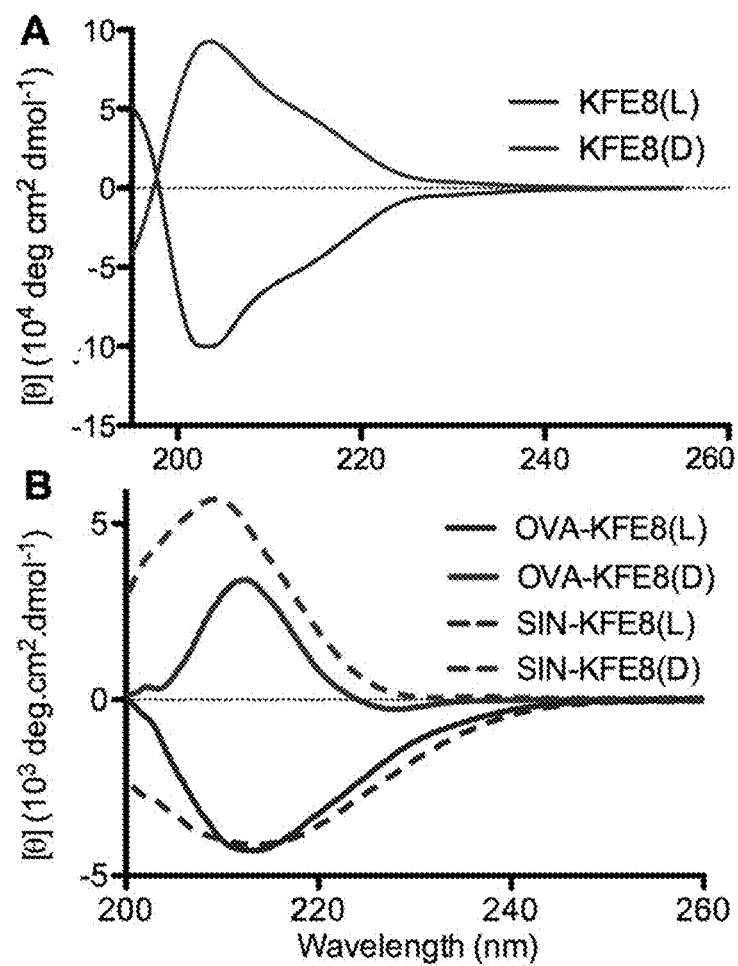
FIG. 10A-10B. Secondary structures of self-assembling peptide enantiomers. (A) CD spectra of KFE8(L) and KFE8(D) and (B) OVA- or SIN-functionalized KFE8(L) or KFE8(D) showing β-sheet rich secondary structures with opposite optical rotations reflecting their molecular chirality. Peptide concentration was 0.5 mM in ultrapure water.
Figure 11:
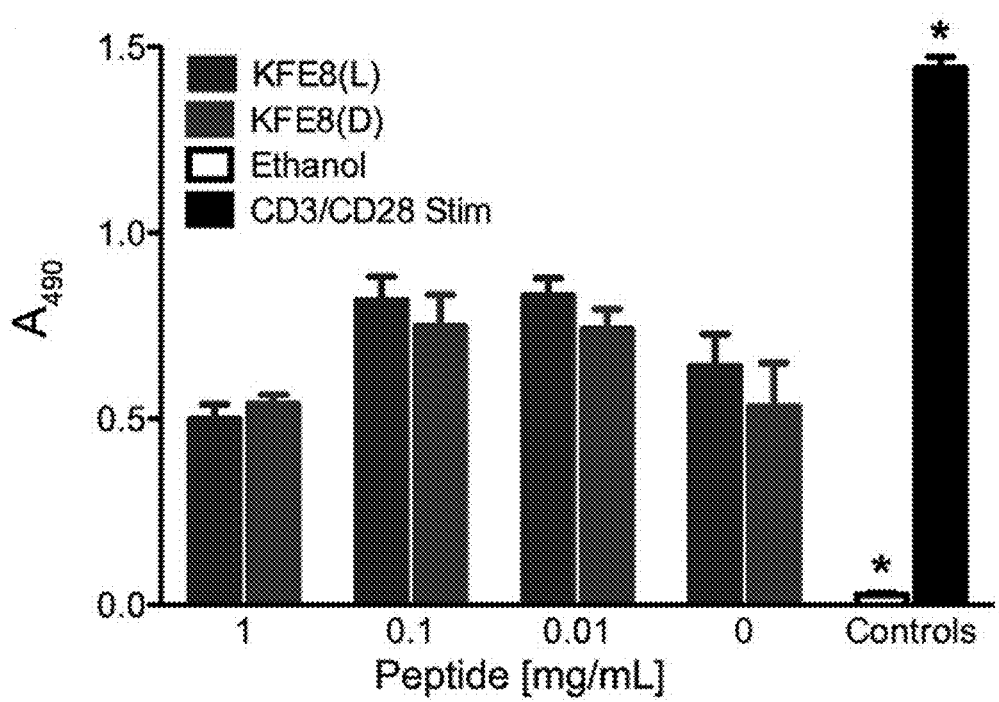
FIG. 11. Cytotoxicity of KFE8(L) and KFE8(D) nanofibers. MTS assay data showing non-cytotoxicity of KFE8(D) nanofibers mouse lymph node cell cultures at different concentrations. Cultures fixed with absolute ethanol or stimulated with anti-CD3 and CD28 antibodies are shown as controls. *$p<0.05$ by ANOVA using Tukey post-hoc test.

Peptide design and assembly. OVA (aa 323-339 of chicken egg ovalbumin) is a MHC-Class II (I-A$^b$)-restricted epitope with a B cell determinant and antibody responses to self-assembling peptide nanofibers bearing OVA have been shown to be entirely CD4 T cell dependent (Rudra, et al., 2012). The CD8 T cell epitope, SIN (aa 257-264 of chicken egg ovalbumin) is a MHC-Class I (H-2K$^b$-restricted epitope and known to elicit strong effector and memory CD8 T cell responses in mice when coupled to self-assembling peptides (Chesson, et al., 2013). The OVA epitope was conjugated to the N-terminus of the enantiomers via a SGSG (SEQ ID NO: 61) linker (FIG. 8A) and the SIN epitope was conjugated to the C-terminus of the enantiomers via a GGAAY linker (SEQ ID NO: 60) (FIG. 8B) (Chesson, et al., 2013; Rudra, et al., 2012). By TEM, it was observed that KFE8(L) and KFE8(D) assembled into nanofibers (FIGS. 9A-9B) and retained their ability to assemble when functionalized with OVA or SIN peptide epitopes on their N- or C-terminus (FIG. 9C to FIG. 9F). Secondary structure analysis of the enantiomers indicated equal and opposite optical rotations, reflecting their molecular chirality with signals at 218 nm (β-sheet secondary structure) and 205 nm (from π-π effects of Phe aromatic groups) (FIG. 10A) (Swanekamp, et al., 2012). Optical rotations of OVA and SIN functionalized enantiomers were also found to be equal and opposite suggesting that the addition of unstructured L amino acid epitopes on either termini did not significantly affect self-assembly (FIG. 10B). L amino acid self-assembling peptides have been found to be non-cytotoxic in cultures of primary cells (Jung, et al., 2009) whereas D amino acids like D-Ala and D-Asp have been reported to be cytotoxic and inhibit cell proliferation (Fisher, et al., 1991). To facilitate the interpretation of the immunological outcomes without significant concerns for cytotoxicity, peptides KFE8(L) or KFE8(D) were added to mouse lymph node cell cultures at concentrations of 0.01, 0.1, or 1 mg/mL and incubated for 24 h. Cells fixed with absolute ethanol or stimulated with anti-CD3 and CD28 antibodies were used as negative and positive controls respectively. No significant differences in cytotoxicity were found between the enantiomers at any concentrations tested (FIG. 10C).

Figures 12A, 12B:
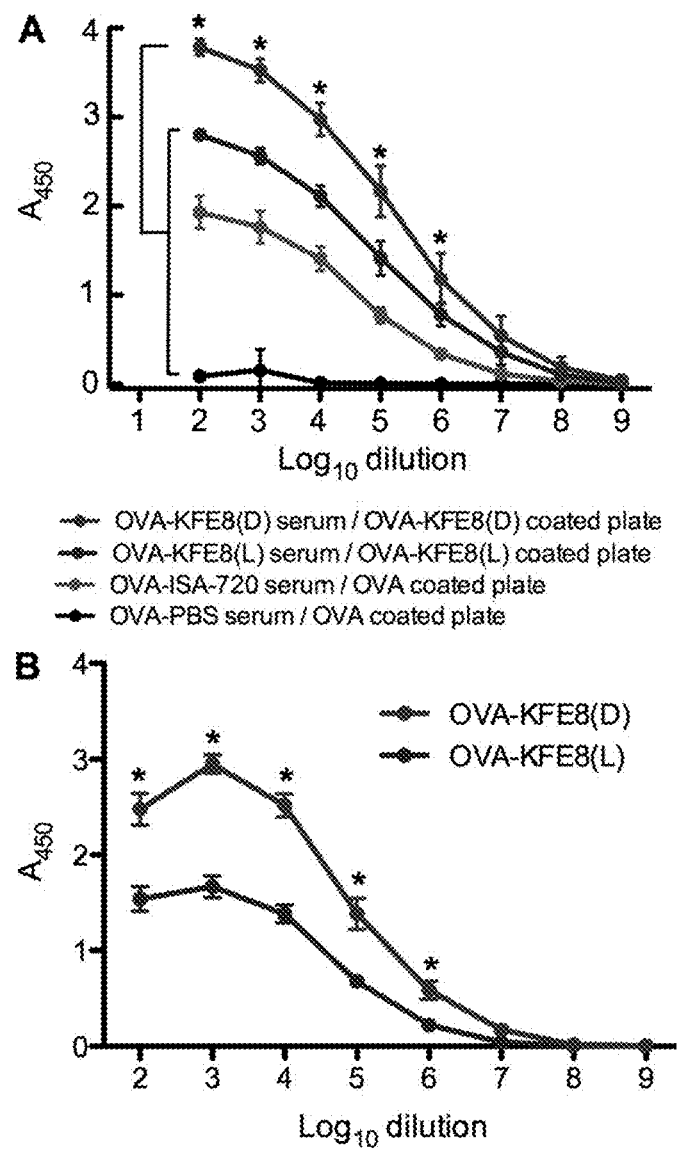
FIG. 12A-12B. Self-assembling D amino acid peptide nanofibers act as immune adjuvants and elicit strong antibody responses. (A) Significantly higher levels of total IgG were detected in the sera of mice immunized with OVA-KFE8(D) nanofibers compared to OVA-KFE8(L) nanofibers or controls. (B) Data showing significantly higher levels of OVA-specific antibodies in the sera of mice immunized with OVA-KFE8(D) nanofibers compared to OVA-KFE8(L) nanofibers where absorbance from control wells coated with SGSG-KFE8(L) or SGSG-KFE8(D) was subtracted to account for contribution from the linker-fiber region. Data is cumulative of three independent experiments (n=3-5 mice per group per experiment). *p<0.05 by ANOVA using Tukey post-hoc test.
Figures 15A, 15B:
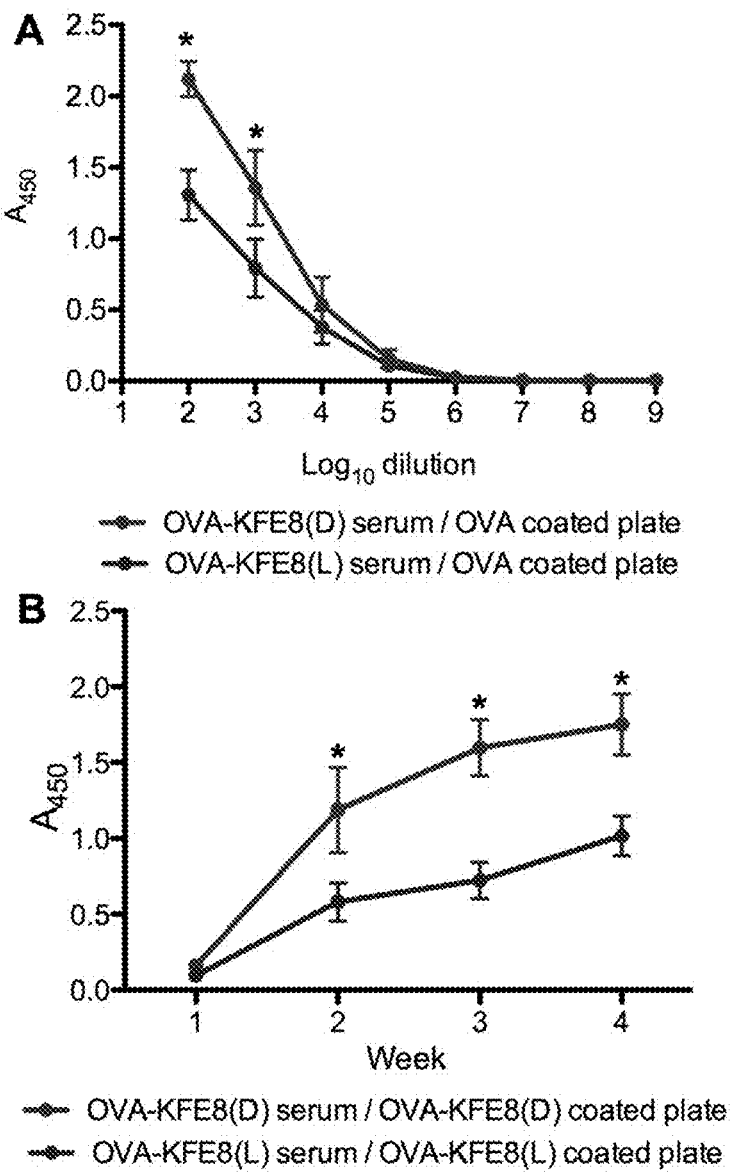
FIG. 15A-15B. D amino acid nanofibers elicit stronger antibody responses compared to L amino acid nanofibers. (A) Significantly higher levels of antibodies were detected in the sera of mice immunized with OVA-KFE8(D) nanofibers on plates coated with the free OVA peptide. (B) Higher levels of antibodies were detected in the sera of mice immunized with OVA-KFE8(D) nanofibers pre-boost. *p<0.05 by ANOVA using Tukey post-hoc test.

D-form self-assembling peptides elicit stronger antibody responses. Mice were immunized and boosted subcutaneously with OVA-KFE8(L) or OVA-KFE8(D) nanofibers and antibody responses were evaluated by ELISA (Rudra, et al., 2012; Huang, et al., 2012; Bowerman, et al., 2012). Sera from mice immunized with OVA-KFE8(L) or OVA-KFE8 (D) were applied to plates coated with the antigenic enantiomers and sera from control groups were applied to plates coated with the free OVA-peptide. OVA-KFE8(D) nanofibers raised robust antibody responses demonstrating that self-assembling peptide domains composed of all D amino acids can adjuvant effectively (FIG. 12A). Interestingly, antibody levels in mice immunized with OVA-KFE8 (D) nanofibers were significantly higher in a series of serum dilutions compared to OVA-KFE8(L) nanofibers or OVA in ISA-720 adjuvant and OVA delivered in PBS did not raise any detectable IgG, as expected (FIG. 12A). This suggests that D amino acid peptide nanofibers elicit stronger antibody responses compared to L amino acid peptide nanofibers. To preclude the effects of the linker-fiber regions, ELISA's were conducted with wells coated with the antigenic enantiomers and control wells coated with nanofibers of SGSG-KFE8(L or D). The signal from the control wells was subtracted from wells coated with the antigenic enantiomers to ascertain the levels of antigen-specific antibodies. Data indicated significantly higher levels of antibodies in the sera of mice immunized with OVA-KFE8(D) nanofibers compared to OVA-KFE8(L) nanofibers (FIG. 12B). Also, when serum from mice immunized with the enantiomers was applied to plates coated with the free OVA peptide, higher levels of anti-OVA antibodies were observed in the sera of mice vaccinated with OVA-KFE8(D) nanofibers compared to OVA-KFE8(L) (FIG. 15A). To confirm that higher antibody levels observed with OVA-KFE8(D) nanofibers were not due to strong recall responses following the booster shot, we compared antibody levels between the antigenic enantiomers pre-boost. ELISA data indicated significantly higher levels of antibodies in mice vaccinated with OVA-KFE8(D) nanofibers starting at week 2 and up to the boost at week 4 compared with mice vaccinated with OVA-KFE8 (L) nanofibers (FIG. 15B). Taken together, the data indicate that D amino acid peptide nanofibers elicit significantly stronger antibody responses in mice compared to L amino acid peptide nanofibers.

Figure 13:
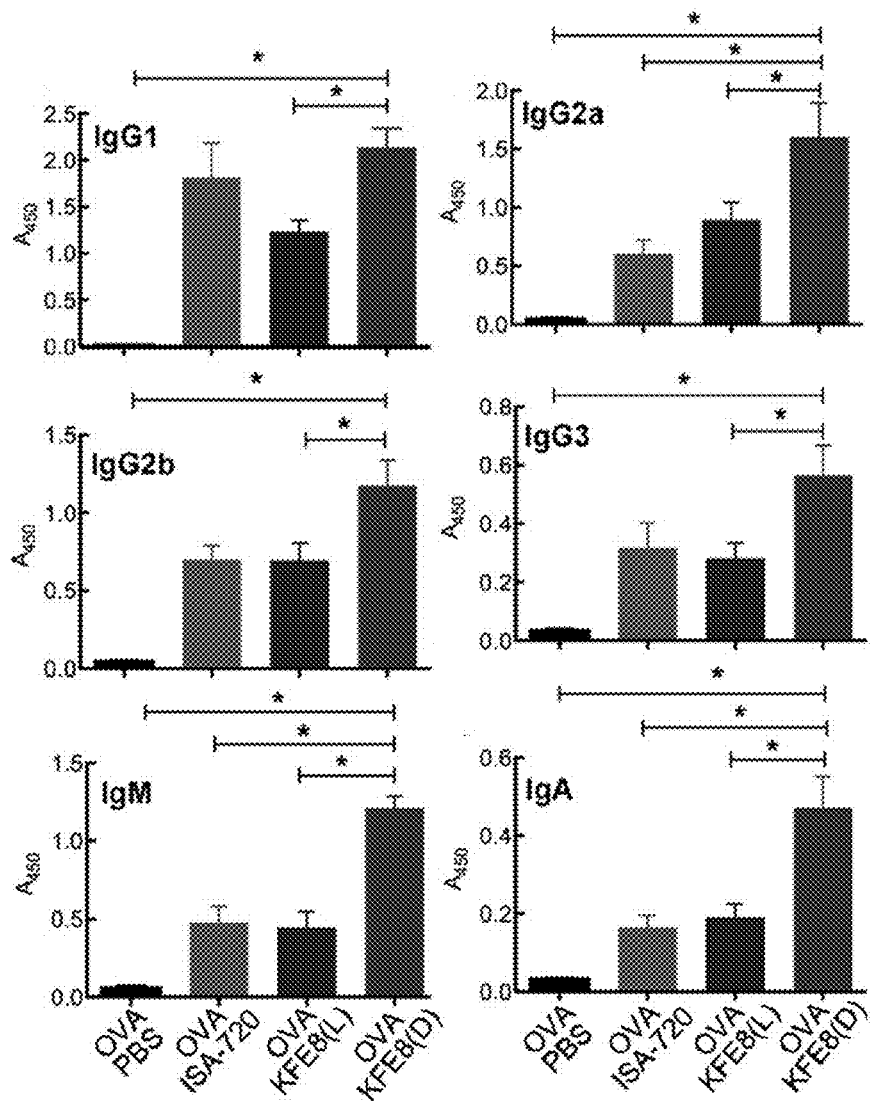
FIG. 13. Antibody isotypes in sera from mice immunized with the enantiomers. Significantly higher levels of all antibody isotypes are detected in the sera of mice immunized with OVA-KFE8(D) nanofibers compared to OVA-KFE8(L) nanofibers. Data is cumulative of three independent experiments (n=3-5 mice per group per experiment). *p<0.05 by ANOVA using Tukey post-hoc test.

D-form self-assembling peptides do not affect the nature of the antibody response. To determine the nature of the immune response elicited by the enantiomers, antibody isotypes were evaluated. All isotypes were evaluated by coating the plates with the free OVA peptide to preclude fiber and linker contributions and enable a direct comparison of isotype levels. For both L and D nanofibers the dominant isotype found was IgG1. Isotypes IgG2a, IgG2b, IgG3, IgM, and IgA were also produced by both enantiomers and were significantly higher in the OVA-KFE8(D) group compared to OVA-KFE8(L) (FIG. 13). The production of IgG2a, IgM, and IgA was also significantly higher in the OVA-KFE8(D) group compared to OVA in ISA-720 (FIG. 13). Taken, together these results indicate that D-amino acid peptide nanofibers do not affect the nature of the immune response.

Figures 14A, 14B, 14C, 14D:
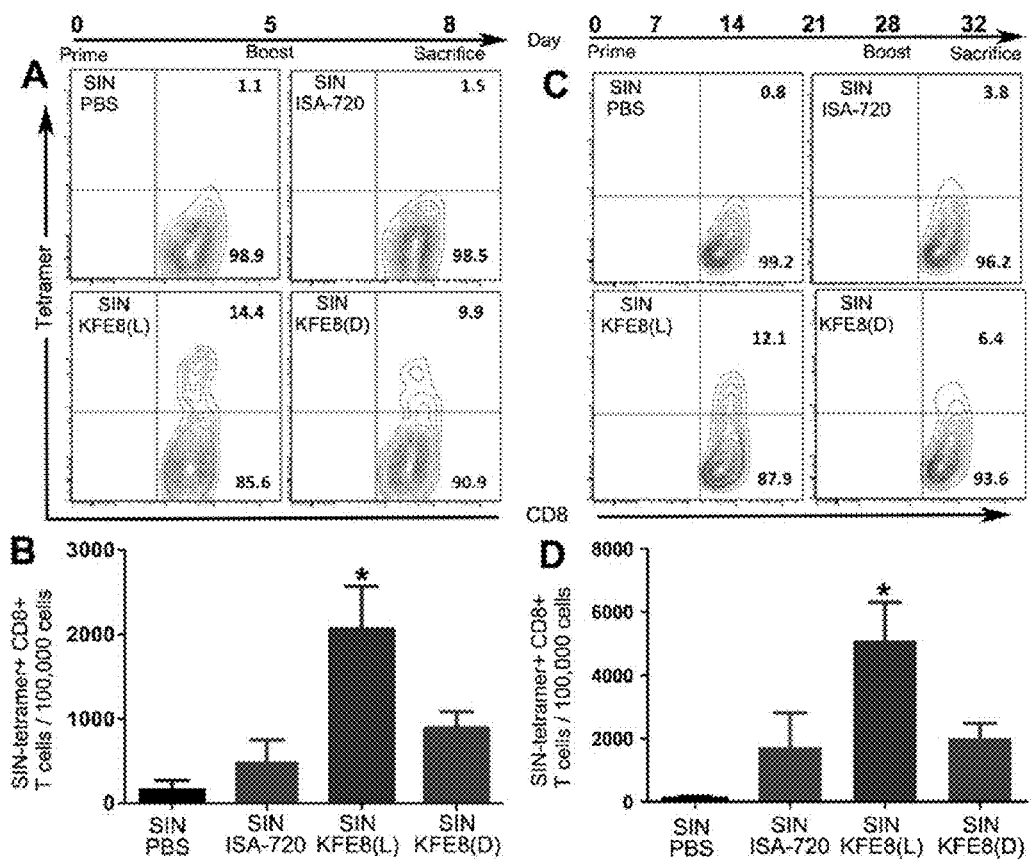
FIG. 14A-14D. Self-assembling peptides composed of D amino acids suppress CD8 T cell responses. (A, C) Flow cytometry plots and (B, D) cumulative bar graphs showing that SIN-KFE8(L) nanofibers elicit robust effector and memory CD8+ T cell responses and generate higher numbers of tetramer+CD8 T cells compared to SIN-KFE8(D) nanofibers. Data is cumulative of three independent experiments (n=3 mice per group per experiment). *p<0.05 by ANOVA using Tukey post-hoc test.

D-form self-assembling peptides elicit weaker CD8 T cell responses. CD8 T cell responses were investigated by immunizing mice in the footpad with nanofibers of SIN-KFE8(L) or SIN-KFE8(D) and determining the numbers of antigen-specific T cells in the draining lymph nodes. For effector CD8 T cell responses, mice were immunized and boosted on day 5, and the numbers of antigen-specific T cells in the draining lymph nodes were evaluated on day 8. We hypothesized that nanofibers composed of D amino acids would also enhance CD8 T cell responses but surprisingly, mice immunized with SIN-KFE8(D) nanofibers had significantly lower numbers of antigen-specific T cells in their draining lymph nodes compared to mice immunized with SIN-KFE8 (L) nanofibers (FIG. 14A). To investigate whether the poor CD8 T cell effector responses were transient, long-term memory responses were investigated by priming mice with the enantiomers followed by a boost at day 28. On day 32 significantly higher numbers of antigen-specific T cells were again observed in the lymph nodes of mice immunized with SIN-KFE8(L) nanofibers (FIG. 14B), confirming that D amino acid nanofibers elicit weaker CD8 T cell responses compared to L amino acid nanofibers.

Figures 16A, 16B, 16C, 16D:
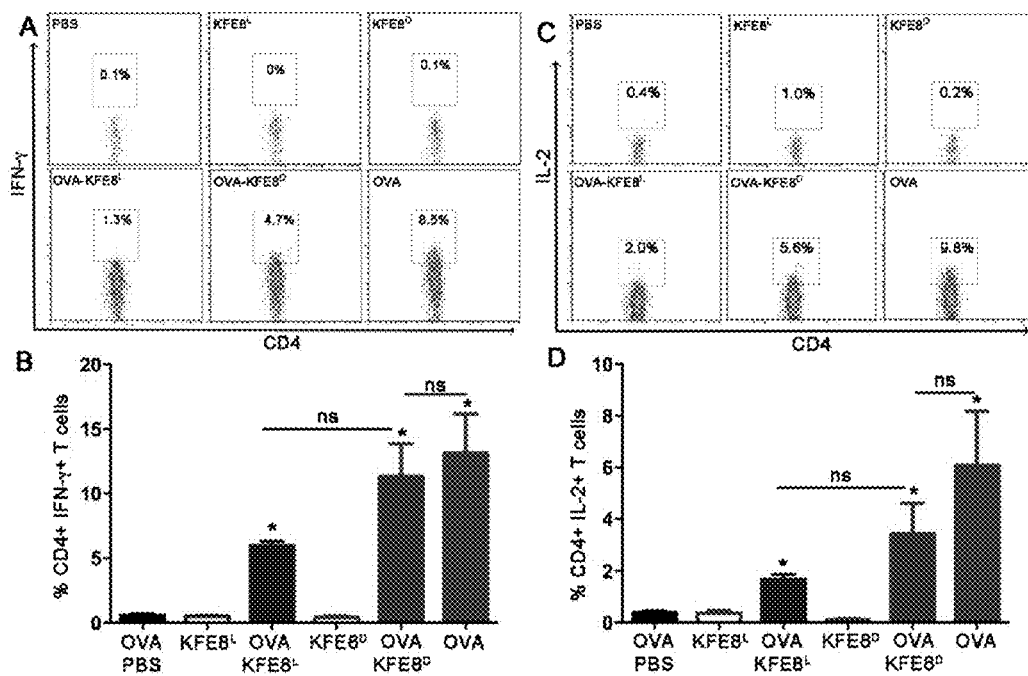
FIG. 16A-16D. OVA-bearing KFE8 enantiomers elicit equivalent activation of CD4+ T helper cells and induce the production of cytokines Whole lymphocyte extracts (containing antigen-presenting cells, B cells, and CD4+ T cell populations) from inguinal, axial, and brachial lymph nodes of OT-II mice were added to plates coated with OVA-KFE8L or OVA-KFE8D nanofibers. Flow cytometry plots showing (A, B) IFN-γ and (C, D) IL-2 production after 6 h stimulation. Bare nanofibers without OVA did not induce any cytokine production. Plates coated with free OVA peptide or PBS were used as positive and negative controls, respectively. Data are representative of one of three experiments conducted with similar results (n=3 mice per group per experiment). n.s.=not significant. *p<0.05 by ANOVA using Tukey posthoc comparison compared to OVA-PBS.

OVA-KFE8D Nanofibers Induce Robust CD4 T Helper Cell Responses. OVA (ISQAVHAAHAEINEAGR) (SEQ ID NO: 26), is a well-characterized CD4+ T helper epitope, a portion of which is also recognized by B cells (ISQAVHAAHA) (SEQ ID NO: 58) (Robertson, et al., 2000). Therefore, immunization with OVA leads to both CD4+ T cell activation and antibody production and studies have shown that antibody responses against OVA are CD4+ T celldependent (Rudra, et al., 2012; Robertson, et al., 2000). To assess whether the enantiomeric nature of nanofibers that contributed to enhanced antibody responses also leads to differential CD4+ T helper cell functionality, we utilized transgenic mice (OT-II mice) that have CD4+ T cells (OT-II cells) whose receptors recognize OVA in the context of MHC-class II molecules.30 CD4+ T cell responses were assessed using an in vitro activation assay. Whole lymphocyte extracts (containing antigen-presenting cell, B cell, and CD4+ T cell populations) from OT-II mice were cultured in wells coated with OVA-bearing enantiomers, and 6 h later the production of cytokines IFN-γ and IL-2 were measured using flow cytometry. Lymphocytes stimulated with PBS or free OVA peptide were used as negative and positive controls, respectively. Data indicated OT-II cells cultured in wells coated with the OVA-bearing enantiomers produced significantly higher levels of IFN-γ (FIGS. 16A, B) and IL-2 (FIGS. 16C, D) compared to wells coated with PBS or bare nanofibers. Also, no significant differences were observed in the levels of IFN-γ and IL-2 production between the enantiomers suggesting equivalent levels of activation (FIG. 16). Furthermore, no cytokine production was observed in wells coated with KFE8L or KFE8D nanofibers, suggesting that enantiomers themselves, without OVA, do not induce nonspecific activation (FIG. 16). Taken together, these data suggest that OVA-KFE8D and OVAKFE8L nanofibers are efficient at eliciting CD4+ T cell responses and that the stereochemistry of the self-assembling domain does not significantly alter cytokine production by CD4+ T cells.

Figures 17A, 17B:
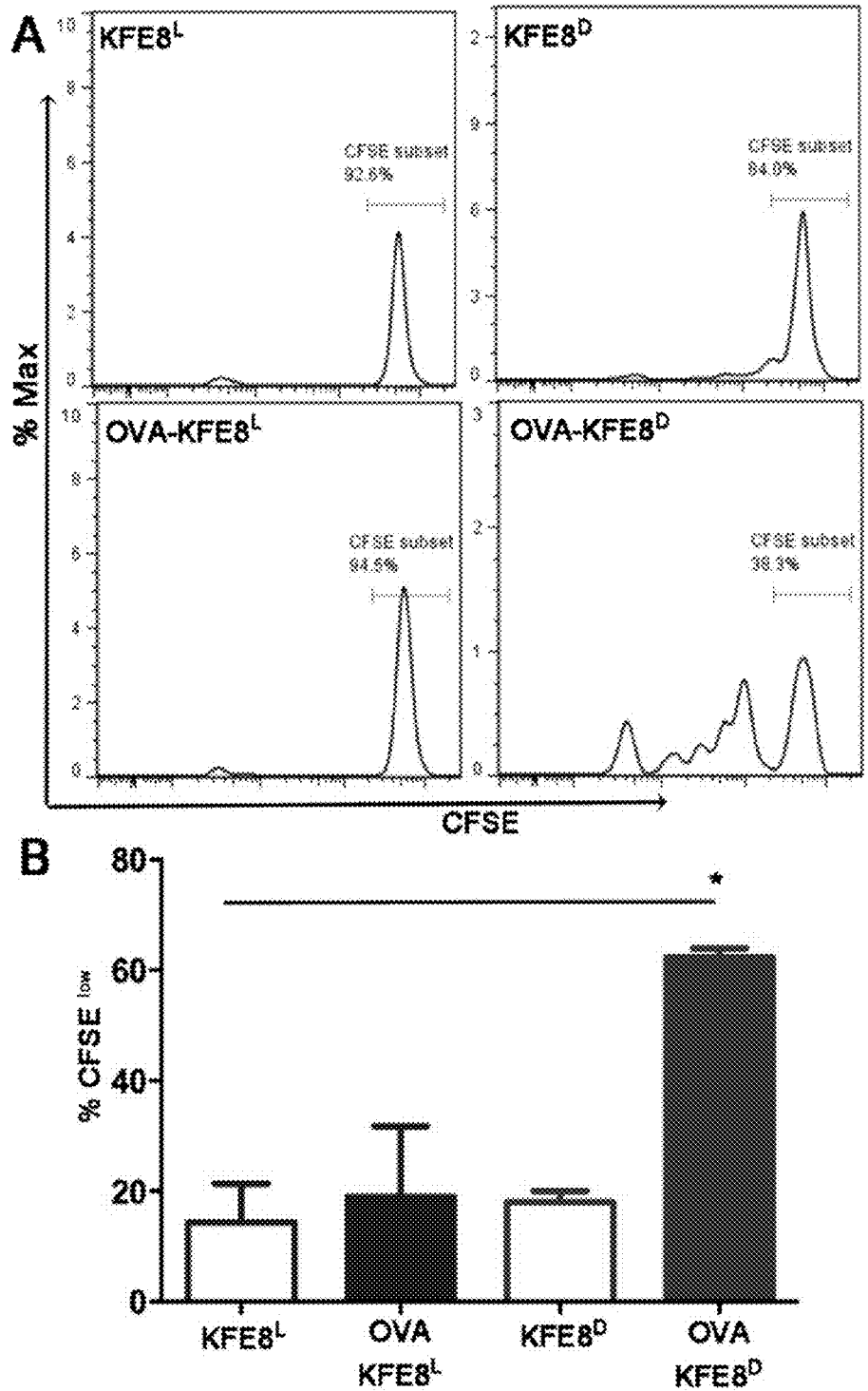
FIG. 17A-17B. In vivo proliferation of CFSE-labeled DTII cells (OVA-specific T cells) after immunization with OVA-bearing enantiomers in the footpad. (A) Representative flow plots showing the proliferation of adoptively transferred-OTII cells into footpads of mice vaccinated with OVA-KFE8D or OVA-KFE8L nanofibers a week earlier. (B) Cumulative figure showing significantly higher percentage of proliferating CFSE-labeled OTII cells in the draining lymph nodes of mice immunized with OVA-KFE8D nanofibers suggesting prolonged antigen presentation. (n=3 mice per group). *p<0.05, by ANOVA using Tukey posthoc comparison.

OVA-KFE8D Nanofibers Prolong Antigen Presentation at the Immunization Site. Previous studies from our lab have shown that peptide nanofiber vaccines (all L-amino acids) are cleared from the immunization site as early as 10 days after vaccination compared to depot forming adjuvants (Chesson, et al., 2014). To investigate whether the reduced proteolytic susceptibility of D-amino acid peptides prolongs antigen-presentation at the immunization site, we used adoptive transfer experiments where mice were injected at the immunization site with CFSElabeled OT-II cells (OVA-specific CD4+ T cells) and measured proliferation of the OT-II cells (in response to existing antigen) via the dilution of the CFSE label using flow cytometry. For these studies, immunizations and adoptive transfers were done in the footpads to maximize antigen depot-OT-II CD4+ T cell interaction and easy collection of draining lymph nodes. Mice were immunized with OVA-KFE8L or OVA-KFE8D nanofibers and a week later CFSE-labeled OT-II cells were transferred at the vaccination site. Twenty-four hours later, mice were sacrificed and draining lymph nodes were extracted. Robust proliferation of OT-II CD4+ T cells was observed in mice vaccinated with OVA-KFE8D nanofibers, as indicated by the dilution of the CFSE label (FIG. 17A). Quantification of the shift in the CFSE intensity indicated that more than 60% of the transferred cells in the OVA-KFE8D nanofiber group had proliferated (FIG. 17B). In contrast, only background levels of proliferation were observed in mice vaccinated with OVAKFE8L nanofibers (FIG. 17A, B). Taken together, these data clearly indicated that OVA-KFE8D nanofibers prolong antigen presentation at the immunization site compared to their Lamino acid counterparts.

Transmission Electron Microscopy (TEM). Stock solutions of 1 mM peptides were allowed to fibrillize in water overnight at 4° C., diluted in PBS to 0.3 mM and applied to 400 mesh copper grids with carbon support film. The grids were negatively stained with 2% uranyl acetate, and imaged on a JEOL EM1400 TEM equipped with $LaB_6$ electron gun and digital cameras. Images were viewed and recorded with an Orius Ultrascan 1000 camera. Scale bar is 50 nm.

Circular dichroism Spectroscopy (CD). CD experiments were carried out on a JASCO J-815 CD Spectrometer. 1 mM peptide stock solutions were made in ultra pure water and diluted to working concentrations before use. CD wavelength range was from 260 nm to 195 nm with a scanning speed of 0.3 nm/s and a bandwidth of 0.5 nm. CD spectra were recorded at room temperature with a fixed-path-length (1 mm) cell. The solvent background contribution was subtracted and resultant CD signal was converted to mean residue ellipticity.

Cytotoxicity Assay. A standard MTS assay was utilized to determine peptide cytotoxicity (Promega, Madison, Wis., cat# G3582). Mouse lymphocytes (B6 mice, 100,000 cells/well) were seeded in 96-well plates in culture media (1640 RPMI containing 1% penicillin/streptomycin, 2% L-glutamine, and 10% FBS) containing 0.01, 0.1 or 1 mg/mL of KFE8(L) or KFE8(D) peptide. The cells were incubated for 24h and the medium was replaced. MTS reagent was applied for 4 h and absorbance at 490 nm was measured using a microplate reader. Controls included cultures fixed with absolute ethanol or treated with 5 µg/ml anti-CD3 and 1 µg/ml CD28 antibodies. All groups contained 3 replicates.

Animals and Immunizations. Peptides were dissolved in sterile water to 8 mM stock solutions, stored overnight at 4° C., and diluted to working concentration of 2 mM using sterile PBS. Female mice (C57BL/6, 6-8 weeks old) were purchased from Taconic Farms. To investigate antibody responses, 50 µl of OVA-KFE8(L) or OVA-KFE8(D) peptide solution (100 nm of antigen) were injected subcutaneously in the flank at two different sites. Mice were boosted on day 28 with two 25 µl injections of peptide solution or controls (50 nmol of antigen) and sacrificed on day 42. Blood was collected weekly via the submandibular vein and sera stored at −80° C. To investigate CD8 T cell responses, mice we immunized in the footpad with 20 µl of SIN-KFE8 (L) or SIN-KFE8(D) peptide solution, boosted on day 5, and sacrificed on day 8 (for effector responses) or boosted on day 28 and sacrificed on day 32 (for memory responses). Mice immunized with OVA or SIN peptides in PBS or ISA-720 adjuvant were used as controls. ISA-720 emulsion was prepared by mixing equal volumes of peptide solution and adjuvant immediately prior to immunization. All experiments were conducted under approved protocols by the University of Texas Medical Branch Institutional Animal Care and Use Committee and repeated independently 3 times with 3-5 mice per group per experiment.

Antibody Responses. High-binding ELISA plates (eBioscience) were coated with 20 µg/mL of antigen in PBS overnight at 4° C. and blocked with 200 µL of 1% BSA in PBST (0.5% Tween-20 in PBS) for 1 h. Serum dilutions were applied ($1:10^{-2}$ to $1:10^{-9}$, 100 µL/well) for 1 h at room temperature followed by peroxidase-conjugated goat anti-mouse IgG (H+L) (Jackson Immuno Research) (1:5000 in 1% BSA-PBST, 100 µL/well). Plates were developed using TMB substrate (100 µL/well, eBioscience), the reaction stopped using 50 µl of 1 M phosphoric acid, and absorbance measured at 450 nm. Absorbance values of PBS (no antigen) coated wells were subtracted to account for background. Antibody isotypes were determined using a mouse monoclonal antibody kit (Sigma, MO) with secondary goat anti-mouse IgG1, IgG2a, IgG2b, IgG3, IgM, and IgA.

CD8 T cell Responses. Lymphocytes were harvested from the ipsilateral inguinal and popliteal draining lymph nodes for effector and memory response studies. Pooled lymph nodes were pressed through a 70 µm cell strainer (BD Biosciences, CA) and washed twice with 1640 RPMI containing 1% penicillin/streptomycin, 2% L-glutamine, and 10% FBS. SIINFEKL (SEQ ID NO: 59) MHC class I tetramer and cell surface marker staining was performed according to standard protocols described previously (Chesson, et al., 2013). H2Kb-OVA tetramer (PE) was purchased from Medical Biological Laboratories (Woburn, Mass.). Live/dead stain (eF506), CD3 (Pacific Blue), CD8 (APC-Cy7), CD44 (PerCPCy5.5) and CD62L (FITC) were purchased from BD Biosciences (San Jose, Calif.). Flow cytometry was performed using a BD FACS Canto II flow cytometer and data were analyzed using FlowJo software (Tree Star, OR).

Statistical Analysis. All the experimental data were plotted using Prism software and represented as mean±SEM, and statistical analysis was performed by ANOVA with Tukey's post hoc test. Statistical significance was assigned at p values <0.05.

REFERENCES

The following references, to the extent that they provide exemplary procedural or other details supplementary to those set forth herein, are specifically incorporated herein by reference.

U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 6,651,655
U.S. Pat. No. 6,733,754
U.S. Pat. No. 6,793,923
Aggeli et al., *Nature*, 386:259-262, 1997.
Armstrong, et al., *Chirality* 1993; 5(5):375-78.
Baumjohann, et al., *Immunity* 2013; 38(3):596-605.
Benkirane, et al., *J Biol Chem* 1993; 268(35):26279-85.
Bettahi et al., *Cancer Immunol. Immunother.*, 58:187-200, 2009.
Billard, et al., *Amino Acids* 2012; 43(5):1851-60.
Bowerman, et al., *Biopolymers* 2012; 98(3):169-84.
Cao et al., *Neurosci.*, 9:25, 2008.
Chen, et al., *Biomaterials* 2013; 34(34):8776-85.
Chesson, et al., *Vaccine* 2013; in press.
Collier and Messersmith, *Bioconjug. Chem.*, 14:748-755, 2003.
Collier, et al., *Chem Soc Rev* 2010; 39(9):3413-24.
Collier, *Soft Matter*, 4:2310-2315, 2008.
Daftarian et al., *Vaccine*, 24:5235-5244, 2006.
Davis et al., *Circulation*, 111:442-450, 2005.
Dubois et al., *J. Biomed. Mater. Res. B Appl. Biomater.*, 87:222-228, 2008.
Eisenbarth, et al., *Nature* 2008; 453(7198):1122-6.
Fisher, et al., *Brain Res Bull* 1991; 26(6):983-85.
Friedman M, Levin, *Amino Acids* 2012; 42(5):1553-82.
Friedman, *Chem Biodivers* 2010; 7(6):1491-1530.
Genove et al., *Biomaterials*, 26:3341-3351, 2005.
Gras et al., *Biomaterials*, 29:1553-1562, 2008.
Guler et al., *Biomacromolecules*, 7:1855-1863, 2006.
Hailemichael, et al., *Nat Med* 2013; 19(4):465-72.
Halle, et al., *Nat Immunol* 2008; 9(8):857-65.
Hartgerink et al., *Science*, 294:1684-1688, 2001.
Holmes et al., *Proc. Natl. Acad. Sci. USA*, 97:6728-6733, 2000.
Horii et al., *PLoS ONE*:2:e190, 2007.
Hsieh et al., *J. Clin. Invest.*, 116:237-248, 2006.
Huang, et al., *JAm Chem Soc* 2012; 134(21):8730-33.
Hudalla, et al., *Adv Healthc Mater* 2013; 2(8):1114-19.
Ishii and Akira, *J. Clin. Immunol.*, 27:363-371, 2007.
Jung et al., *Biomaterials*, 29:2143-2151, 2008.
Jung et al., *Biomaterials*, 30:2400-2410, 2009.
Lambrecht et al., *Curr. Opin. Immunol.*, 21:23-29, 2009.
Luo, et al., *Biomaterials* 2011; 32(8):2013-20.
Luo, et al., *Biomaterials* 2013; 34(21):4902-13.
Luo, et al., *Chem Soc Rev* 2012; 41(13):4736-54.
Luo, et al., *Macromol Biosci* 2008; 8(8):785-91.
Luo, et al., *PloS ONE* 2008; 3(5):e2364.
Lutolf and Hubbell, *Nat. Biotechnol.*, 23:47-55, 2005.
Malyala & Singh, *J Pharm Sci* 2008; 97(6):2041-44.
Maraskovsky et al., *Immunol. Cell Biol.*, 87:371-376, 2009.
Marrack et al., *Nat. Rev. Immunol.*, 9:287-293, 2009.
Maude, et al., *Nanomedicine* 2013; 8(5):823-47.
McKee et al., *Immunity*, 27:687-690, 2007.
McSorley et al., *J. Immunol.*, 169:3914-3919, 2002.
Montero, et al., *Chem Biol* 2011; 18(11):1453-62.
Nagy, et al., *J Am Chem Soc* 2011; 133(38):14975-77.
O'Hagan, et al., *Drug Discov Today* 2009; 14(11-12):541-51.
Place et al., *Nat. Mater.*, 8:457-470, 2009.
Purcell et al., *Nat. Rev. Drug Discov.*, 6:404-414, 2007.
Remington's Pharmaceutical Sciences, 15th Ed., 1035-1038 and 1570-1580, 1990.
Riley et al., *Biotechnol. Bioeng.*, 103:241-251, 2009.
Rudra, et al., *ACS Nano* 2012; 6(2):1557-64.
Rudra, et al., *Biomaterials* 2012; 33(27):6476-84.

Rudra, et al., *Proc Natl Acad Sci USA* 2010; 107(2):622-67.
Schneider et al., *J. Am. Chem. Soc.*, 124:15030-15037, 2002.
Sela & Zisman, *FASEB J* 1997; 11(6):449-56.
Silva et al., *Science*, 303:1352-1355, 2004.
Sun et al., *Vaccine*, 27:1787-1796, 2009.
Sun, et al., *JAm Chem Soc* 2007; 129(6):1496-7.
Swanekamp, et al., *JAm Chem Soc* 2012; 134(12):5556-59.
Toth et al., *Int. J. Pept. Res. Ther.*, 14:333-340, 2008.
Tysseling-Mattiace et al., *J. Neurosci.*, 28:3814-3823, 2008.
Wendorf et al., *J. Pharm. Sci.*, 95:2738-2750, 2006.
Yang and Mine, *Biochem. Biophys. Res. Commun.*, 378:203-208, 2009.
Zagon, et al., *Nutr Res* 1994; 14(3):445-63.
Zhou et al., *Biomaterials*, 30:2523-2530, 2009.

What is claimed is:

1. An immunogenic composition comprising a peptide fibril coupled to at least one antigen that is presented multiple times on the peptide fibril, wherein the peptide fibril comprises two or more of a self-assembling peptide, the self-assembling peptide comprising an amino acid sequence of FKFEFKFE (SEQ ID NO: 25); QQKFQFQFEQQ (SEQ ID NO: 1); KFQFQFE (SEQ ID NO: 2); QQRFQFQFEQQ (SEQ ID NO: 3); QQRFQWQFEQQ (SEQ ID NO: 4); FEFEFKFKFEFEFKFK (SEQ ID NO: 5); QQRFEWEFEQQ (SEQ ID NO: 6); QQXFXWXFQQQ (where X denotes ornithine) (SEQ ID NO: 7); FKFEFKFEFKFE (SEQ ID NO: 8); FKFQFKFQFKFQ (SEQ ID NO: 9); AEAKAEAKAEAKAEAK (SEQ ID NO: 10); AEAEAKAKAEAEAKAK (SEQ ID NO: 11); AEAEAEAEAKAKAKAK (SEQ ID NO: 12); RADARADARADARADA (SEQ ID NO: 13); RARADADARARADADA (SEQ ID NO: 14); SGRGYBLGGQGAGAAAAGGAGQGGYGGLGSQG (SEQ ID NO: 15); EWEXEXEXEX (where X=V, A, S, or P) (SEQ ID NO: 16); WKXKXKXKXK (where X=V, A, S, or P) (SEQ ID NO: 17); KWKVKVKVKVKVK (where X=V, A, S, or P) (SEQ ID NO: 18); LLLLKKKKKKKKLLLL (SEQ ID NO: 19); VKVKVKVKVDPPTKVKVKVKV (SEQ ID NO: 20); VKVKVKVKVDPPTKVKTKVKV (SEQ ID NO: 21); KVKVKVKVKDPPSVKVKVKVK (SEQ ID NO: 22); VKVKVKVKVDPPSKVKVKVKV (SEQ ID NO: 23);or VKVKVKTKVDPPTKVKTKVKV (SEQ ID NO: 24), wherein the self-assembling peptide comprises one or more D amino acids.

2. The composition of claim 1, wherein the self-assembling peptide is FKFEFKFE (SEQ ID NO: 25) and has all D-amino acids.

3. The composition of claim 1, wherein the peptide fibril has a length of at least 0.5 to 100 μm.

4. The composition of claim 1, wherein the peptide fibril has a molecular weight of at least 10,000 da-7×10$^8$ da.

5. The composition of claim 1, wherein the self-assembling peptide is 7 to 40 amino acids in length.

6. The composition of claim 1, wherein the antigens are covalently coupled to the self-assembling peptides.

7. The composition of claim 1, wherein the antigens are covalently coupled to a carboxy terminus, an amino terminus, or the carboxy and amino terminus of the self-assembling peptides.

8. The composition of claim 1, wherein the antigens are T cell and/or B cell epitopes.

9. The composition of claim 1, wherein the antigens are peptides.

10. The composition of claim 1, wherein the antigens are 5 to 20 amino acids in length.

11. The composition of claim 1, wherein the antigens are polypeptides.

12. The composition of claim 1, wherein the antigens are covalently coupled to the peptide fibril via a peptide linker.

13. The composition of claim 12, wherein the peptide linker is SGSG (SEQ ID NO: 61) or GGAAY (SEQ ID NO: 60).

14. The composition of claim 1, wherein the at least one antigen is an OVA epitope of ISQAVHAAHAEINEAGR (SEQ ID NO: 26).

15. The composition of claim 1, wherein the at least one antigen is a SIN epitope of SIINFEKL (SEQ ID NO: 59).

16. The composition of claim 1, wherein all amino acids of the self-assembling peptide are D amino acids.

17. A self-assembling antigen composition comprising an antigen coupled to a fibril-forming peptide, the fibril-forming peptide selected from a peptide having an amino acid sequence of FKFEFKFE (SEQ ID NO: 25); QQKFQFQFEQQ (SEQ ID NO: 1); KFQFQFE (SEQ ID NO: 2); QQRFQFQFEQQ (SEQ ID NO: 3); QQRFQWQFEQQ (SEQ ID NO: 4); FEFEFKFKFEFEFKFK (SEQ ID NO: 5); QQRFEWEFEQQ (SEQ ID NO: 6); QQXFXWXFQQQ (where X denotes ornithine) (SEQ ID NO: 7); FKFEFKFEFKFE (SEQ ID NO: 8); FKFQFKFQFKFQ (SEQ ID NO: 9); AEAKAEAKAEAKAEAK (SEQ ID NO: 10); AEAEAKAKAEAEAKAK (SEQ ID NO: 11); AEAEAEAEAKAKAKAK (SEQ ID NO: 12); RADARADARADARADA (SEQ ID NO: 13); RARADADARARADADA (SEQ ID NO: 14); SGRGYBLGGQGAGAAAAAGGAGQGGYGGLGSQG (SEQ ID NO: 15); EWEXEXEXEX (where X =V, A ,S, or P) (SEQ ID NO: 16); WKXKXKXKXK (where X =V, A, S, or P) (SEQ ID NO: 17); KWKVKVKVKVKVKVK (where X =V, A, S, or P) (SEQ ID NO: 18); LLLLKKKKKKKKLLLL (SEQ ID NO: 19); VKVKVKVKVDPPTKVKVKVKV (SEQ ID NO: 20); VKVKVKVKVDPPTKVKTKVKV (SEQ ID NO: 21); KVKVKVKVKDPPSVKVKVKVK (SEQ ID NO: 22); VKVKVKVKVDPPSKVKVKVKV (SEQ ID NO: 23); or VKVKVKTKVDPPTKVKTKVKV (SEQ ID NO: 24), wherein the fibril-forming peptide has one or more D amino acids.

18. The composition of claim 17, wherein all the amino acids of the fibril-forming peptide are D amino acids.

19. A method of inducing an immune response comprising administering the composition of claim 1 in an amount sufficient to induce an immune response.

* * * * *